(12) United States Patent
Korth

(10) Patent No.: US 11,039,997 B2
(45) Date of Patent: Jun. 22, 2021

(54) COSMETIC, DERMATIC, PROTECTIVE COMPOSITIONS COMPRISING PHOSPHOLIPIDS, LECITHINS WITH PEPTIDES AND AT LEAST ONE ACETYLATING COMPOUND

(71) Applicant: Ruth-Maria Korth, Munich (DE)

(72) Inventor: Ruth-Maria Korth, Munich (DE)

( * ) Notice: Subject to any disclaimer, the term of this patent is extended or adjusted under 35 U.S.C. 154(b) by 764 days.

(21) Appl. No.: 14/121,042

(22) Filed: Jul. 24, 2014

(65) Prior Publication Data

US 2017/0135930 A1    May 18, 2017
US 2019/0380938 A9    Dec. 19, 2019

Related U.S. Application Data

(62) Division of application No. 12/085,468, filed as application No. PCT/DE2006/002294 on Dec. 21, 2006, now Pat. No. 10,517,838.

(30) Foreign Application Priority Data

Dec. 27, 2005 (DE) ............... 10 2005 062 417.0

(51) Int. Cl.
| | | |
|---|---|---|
| A61K 8/49 | (2006.01) | |
| A61Q 17/04 | (2006.01) | |
| A61K 8/55 | (2006.01) | |
| A61K 8/64 | (2006.01) | |
| A61K 8/14 | (2006.01) | |
| A61K 8/36 | (2006.01) | |
| A61K 8/68 | (2006.01) | |
| A61Q 19/02 | (2006.01) | |
| A61Q 19/00 | (2006.01) | |
| A61K 36/00 | (2006.01) | |

(52) U.S. Cl.
CPC .............. *A61K 8/4973* (2013.01); *A61K 8/14* (2013.01); *A61K 8/361* (2013.01); *A61K 8/553* (2013.01); *A61K 8/64* (2013.01); *A61K 8/68* (2013.01); *A61Q 17/04* (2013.01); *A61Q 19/00* (2013.01); *A61Q 19/02* (2013.01); *A61K 36/00* (2013.01); *A61K 2800/59* (2013.01)

(58) Field of Classification Search
CPC ........ A61K 8/4973; A61K 31/00; A61K 8/14; A61K 8/361; A61K 8/68; A61K 8/64; A61K 8/553; A61K 36/00; A61K 2800/59; A61Q 19/02; A61Q 17/04; A61Q 19/00
See application file for complete search history.

(56) References Cited

U.S. PATENT DOCUMENTS

| | | |
|---|---|---|
| 975,483 A | 11/1910 | Turek |
| 5,214,062 A | 5/1993 | Mark et al. |
| 5,346,894 A | 9/1994 | Korth |
| 5,356,791 A | 10/1994 | Korth |
| 5,480,881 A | 1/1996 | Korth |
| 5,530,023 A | 6/1996 | Korth |
| 5,605,927 A * | 2/1997 | Korth .............. A61K 31/00 514/453 |
| 5,696,114 A | 12/1997 | Korth |
| 5,852,052 A | 12/1998 | Korth |
| 5,895,785 A | 4/1999 | Korth |
| 5,976,548 A | 11/1999 | Hsia et al. |
| 6,399,099 B1 | 6/2002 | Oschmann |
| 9,725,483 B2 * | 8/2017 | Garcia Anton ...... C07K 5/1005 |
| 2002/0127287 A1 | 9/2002 | Korth |
| 2004/0180105 A1 | 3/2004 | Drieu |
| 2004/0101578 A1 | 5/2004 | Kim et al. |

FOREIGN PATENT DOCUMENTS

| | | |
|---|---|---|
| DE | 3929763 A1 | 3/1991 |
| DE | 297 00 734 U1 | 6/1997 |
| DE | 2970034 U1 | 6/1997 |
| DE | 10 2005 062 417 A1 | 8/2007 |
| EP | 0303277 A1 | 2/1987 |
| EP | 0459 432 | 5/1991 |
| EP | 459437 | 5/1991 |
| EP | 0648488 B1 | 4/1994 |
| EP | 0604 830 B1 | 7/1994 |
| EP | 0312 913 B2 | 12/1995 |
| EP | 0312 913 B2 | 12/1995 |
| EP | 1037 646 B1 | 9/2000 |
| WO | WO 01/12208 A1 | 2/2001 |
| WO | WO 01/12208 A1 | 2/2001 |

(Continued)

OTHER PUBLICATIONS

R. Korth et al. Comparison of three paf-acether receptor antagonists,Eur. HJ.Pharmacol. 152,pp. 101-110, 1988.
R.Korth et al. Lipoprotein-associated paf (LA-Paf) was found in washes human platelets and monocyte/macrophage-like u937 cells Chem Phys. Lipids 70, pp. 109-119,1994.
Review: Specific receptors of platelet-activating factor, receptor heterogity, and signal transduction mechanisms San-Bao Wang Hwang. J. of Lipid Mediators 2, pp. 123-135, 1990.
C.H.Jacobus, Hypervitaminosis D associated with drinking milk. New Engl. J. Med. vol. 326,pp. 11724-1181, 1992.

(Continued)

*Primary Examiner* — Snigdha Maewall
(74) *Attorney, Agent, or Firm* — Nixon & Vanderhye

(57) ABSTRACT

The invention refers to novel dermatic and cosmetic compositions to protect against impaired pigmentation of the skin. Locally caring Ginkgoloides are selected out of pure, high quality products comprising phospholipids and lecithins to antagonize alkyl-acyl GPC. The Ginkgoloides are bound to one or more transport proteins, carrier proteins, peptides, amino acids and these carriers contain at least one acetyl group and/or Acetyl CoA. The entire transdermal compositions then endocrinologically equilibrate the skin and the skin cells whereby acetylating compounds locally act as sun screening agent.

4 Claims, 7 Drawing Sheets

(56) References Cited

FOREIGN PATENT DOCUMENTS

| WO | WO2005/025507 A1 | 3/2005 |
|---|---|---|
| WO | WO 2005/025587 A1 | 3/2005 |

OTHER PUBLICATIONS

M.D.Garcia et al. Topical antiinflammatory activity of phytosterols isolated from Erngium Foetidum on chronic and inflammation models. Phytother.REs. 13(1), abstract, 1999.

AE Schulte et al. Purification and characterization of mevalonate kinase from suspension-cultured cells of CathaRANTUS ROSEUS: Arch Biochem.378(2),abstract.

S.Watanabe et al. CJ -15,981 and CJ13,982 new squalene inhibitors. J Antibiot. 2001, abstract 2001.

R.Korth et al. Comparison of three paf-acether receptor antagonist ginkgolides,Eur.J.Pharmacol. 152, pp. 101-110, 1998.

R.Korth et al., Lipoprotein-associated paf (LA-paf) was found in washed human platelets and monocyte/macrophage-like 0937 cells. Chem.Phys.Lipids 70, pp. 109-119,1994.

C.H.Jacobus, Hypervitaminosis D associated with drinking milk. New Engl. J.Med.vol. 326, pp. 1174-1181, 1992.

KP Schwabe; Ginkgo biloba leaf extracts with a reduced 4-o methylpyridoxine and biflanoe content. Summary WO1999032129A1 Publ. No. EP1037646B1. Sep. 4, 2002, Google Patents.

MD Garcia et al. Topical antiinflammatory activity of phyto-sterols isolated from Erngium foetidum on chronic and acute inflammation models. Phytother.Res.13(1), abstract,1999,p. 78.

AE Schulte,et al. Purification and characterization of mevalonate kinase from suspension-cultured cells of Catharanthus roseus Arch Biochem Biophys.378(2):abstract 2000;p. 287.

S Watanabe et al. CJ-13,981 and CJ-13,982, new squalene inhibitors J Antibiot.2001, p. 1025, abstract, 2001.

* cited by examiner

COSMETIC, DERMATIC, PROTECTIVE COMPOSITIONS COMPRISING PHOSPHOLIPIDS, LECITHINS WITH PEPTIDES AND AT LEAST ONE ACETYLATING COMPOUND

This is a division of Ser. No. 12/085,468 (filed May 23, 2008), now U.S. Pat. No. 10,517,838 issued Dec. 31, 2019, based on PCT/DE2006/002294 filed Dec. 21, 2006.

1) THE NOVEL COMPOSITIONS OF THE INVENTION

The compositions are novel and fresh and inventive and comprising at least one prehormone, peptide-proteo-hormone, Ginkgoloide, mineral, trace element. Hormonal and/or dietary compositions are used for the first time for a hormonal, determinative equilibration. For the first time, a prehormone, hormone selected out of mevalonates, cholecalciferol-, calcitriol-group and/or the peptide-proteo-hormone group is adjusted with Ginkgoloides. Precursors of hormones (prehormones) by preference out of the "ergocalciferol- (D2), cholecalciferol (D3) group" are mixed for the first time with at least one constituent (e.g. iodide, selene, zinc). Thus, the invention refers to novel compositions for surprising hormonal methods of use against alkyl-, acyl-like destabilisations of cells. The novel compositions contain for the first time a mixture of Ginkgoloides with a mineral as essential constituent.

In addition, a second method of use surprises which is directed against alkyl-acyl-GPC (AAGPC) its derivatives (alkyl-lipids) and/or products (e.g. acetylacyl-coenzyme A, CoA) to protect also acetylcholine (re-) synthesis and the (central) hormones. Ginkgoloides inhibit here the binding of the alkyl-group mediating enrichment of cellular AAGPC by intermediate of LDL. AAGPC is the mother compound of alkyl lipids and of the acyl-, choline groups for determination/impressing therewith the energy balance of all cells. It was developed here for the first time how AAGPC determines e.g. the synthesis of mevalonates and/or how AAGPC inhibits Acetyl-CoA by formation of acetylacyl Coenzym A (CoA) competing for the substrate with acetylcholine (re-) synthesis and/or impairing then that hormones loose strength. The unexpected alkyl-, acyl-like hypersensitivity syndromes of cells, organs, glands, tissues were clinically treated. In addition, the cellular organelles such as cytosol, microsomes, lysosomes, peroxysomes are disturbed and exhausted. Ginkgoloides are combined here for the first time with acetylcysteine to antagonize the hypersensitivity syndromes.

The novel compositions comprising at least one prehormone, hormone and at least one mineral, constituent with Ginkgoloides are used for the manufacture of compounds for oral, dietary and/or local, cosmetic use. The (semi-) synthetic, manufactured components are antioxidatively stabilized and are offered in a united form to the outside.

The alkyl lipids are stable and exert formative influence in a hormonal manner on carrier proteins and on cells in the entire organism. Those alcohol metabolites show unexpected early, significant impairments, as free albumin declines and e.g. hormones and/or lipids become more and more injurious, nearly toxic. The clinical alkyl-related impairments are shown for example using significant associations between alcohol and/or nicotine use with albuminuria, hematuria, diabetic risk, rise of blood pressure and these impairments are even aggravated by hormones. On the contrary, the novel compositions equilibrate and determine in a hormonal manner the entire body. To promote health, the alkyl-like destabilisations were not antagonized, repaired in a "forte . . . intense" manner while clinical impairments were equilibrated, balanced in a hormonal manner whereby the quality of lifestyle behavior was improved leading then to lower noxa uptake. Even severe alcoholic kidney impairments were successfully treated here as shown with an abstinent patient and/or there was healing of a nicotine-mediated hematuria, diabetic risk (Pre-diabetes).

The ratio of albumin to triglycerides significantly declines during alcohol problems or obesity indicating that albumin is carried from inside the vessels out in parallel with rise of blood pressure and decline of skin- subcutaneous- and connective tissue. Albumin of healthy persons represents 60% of all plasma peptides wherein only 40% of the total albumin remains in the plasma and only free albumin is protective. The compositions protect against unclean albumin carrying alkyl lipids and calcium into the tissue, into the brain.

Impairments of pigmentation are recognized as an unexpected problem of the entire organism and those were treated then in a locally acting, hormonal and entire manner. Ginkgoloides with sunscreening agents strengthen all cells and tissues. Only antioxidatively stabilized oils are topically used without ethereal volatile oils (e.g. purified olive oils, *Soja* products etc). The central melanotropic peptide hormones are modulated here and declined by acetylation for example using acetylcysteine, amino acids, peptides, multivitamin compounds. The novel methods of manufacture, screening- and administration of Ginkgoloides were revealed for the first time (in P34669914) wherein novel compositions are enriched and adapted for persons in need using e.g. sun screening agents, minerals, folic acid, proteoglycans, vitamins, constituents for example selene and/or peptides, amino acids, antioxidatively stabilized lipids, phospholipide, lecithin, ceramides, unsaturated fatty acids.

2) THE COMPONENTS 2.1 Adjusting of the mineral metabolism:

The hormonal compositions equilibrate the whole organism. A silent_loss of calcium has been recognized here for the first time using albuminuria to be antagonized in a hormonal manner. The compositions mediate the healing of albuminuria and thus antagonize the silent loss of bone mass by equilibration of the calcium-dependent parathormone (peptide hormone) resulting in binding of phosphor to bones and teeth.

The loss of calcium is calculated here for the first time using albuminuria to be supplemented (0.8 mg calcium per mg albumin pro liter urine). The need of light-dependent hormones, prehormones D2/D3 is about 1000 IU per day and of calcium 600 mg per day. The daily need of iodide is about 150 µg per day, lowers lipids and protects the nervous system. Intake of water and food cannot always cover the surprisingly elevated need of minerals and iodide which is supplemented here. For example, vegetarian persons need more vitamin B12 supplementation. Calcium (calciumcarbonate, calciumcitrate etc), phosphor (phosphate etc) as constituents (iodine, iodide, zinc, selene) are combined with Ginkgoloides for the first time.

The hormones are also adapted for the need and selected out of the group consisting of peptide-proteo-hormones or out of the group comprising dihydroxy-cholecalciferol, calcitriols. The prehormones, phytohormones are selected out of the group comprising dolicholes, mevalonates, isoprenoides, squalens, chinones, farnesyl, cholestanes, aterines (sterol) and those are stabilized, enriched. Those known precursors and/or light-dependent prehormones D2 originate by preference from plants, for example the ergocalciferoles and are composed here with prehormone D3 originating by preference out of the animal-derived group of cholecalciferols (see Harper's Biochemistry, 24th Edition, page 617). Antioxidatively stabilized fish oils and/or plant oils are composed to reach the best, by preference oily dilution of phytohormones, prehormones, vitamins out of the group A,B,C,E, lecithins, unsaturated fatty acids and ceramides, minerals, calcium, iodide, selene, zinc. The light-protected plant oils further contain phytosterines, cholestanes that means the basic hydrocarbons, of all sterines (sterols), ubiquinones (protection of mitochondrions), squalenes etc. as precursors of hormones (phytohormones, prehormones). Free e.g. bovine albumin is added also to supplement vitamin B12. The (semi-) synthetic and/or natural hormones, constituents, Ginkgoloides are composed with compounds, oils and prepared for the special purpose with antioxidatively stabilized, natural and/or (semi-)synthetic products from animal products and plant oils.

For example, an antioxidatively stabilized, concentrated oil from salt water fishes is composed with pumpkin kernel oil and (semi-) synthetic folic acid (e.g. 24 mg/ml, 1/l, vol/vol). The fish oil product contains 35% omega-3-fatty acids with 18% sicosapentaenoic acids (EPA) and 12% docohexaenoic acids and are stabilized using vitamin E (10 mg/1 g, 14.9 I.E.) that means protection against oxidation. The fish oil is selected regarding the portion of prehormones D2+D3 by preference 16 µg/100 g, phosphor e.g. 300 mg/100 g, iodine by preference 8.4 µg per g fish oil. Fish oils also contain unsaturated lecithins (Korth et al. Chem. Phys. Lipids 36, p. 209, 1985), which are also stabilized here in accordance with the present invention for example using selene and/or vitamin B. Prepared, purified, antioxidatively stabilized oils, unsaturated plant oils are by preference used as carriers and contain pre(phyto)hormones, calcium, phosphor, phosphate, unsaturated fatty acids, polyphenoles, lecithin, iodide (e.g. 100 µg).

2.2. Ginkgoloides:

Ginkgoloides share the classical pharmacological regression line for inhibition of the alkyl lipids. The selection of Ginkgoloides e.g. the "manufacturing of gingkolides as mixture" was adapted here for the unexpected clinical use (adapted for medical use). Nevertheless, the "chemically defined extract of *Ginkgo biloba*" is the pharmacological guide substance (Korth et al. Eur. J. Pharmacol. 152, S. 101, 1988; EP 0312913), so that BN 52021 is tested here as representative for all natural Ginkgoloides and WEB2086 is tested as representative for all synthetic Ginkgoloides in examples.

The Ginkgoloides were successfully tested here using novel methods, to be subsequently composed, adjusted, diluted using surprising components (e.g. ⅓, vol/vol) using by preference dry substance diluted with oils or with solutions without alcohol which are commercially available (2:1, v/v) and adapted to persons who are often at risk for alcohol problems. The idea is new to compose, for example Ginkgoloides with iodide and/or sun screening agents as this has not been proposed before in the large number of preparation procedures which, are published before (see P344669914). Ginkgoloides are composed here for the first time e.g. with acetylcysteines, alkali-earthalkali-carbonate, citrate (citrone-wine-acidic acids), leading to a novel composition for sherbet liquids in accordance with the invention. Also a composition of Ginkgoloides with said constituents is novel and inventive.

Furthermore, novel methods of manufacturing and novel screening procedures are specified which are included by citation of P34669914. The novel compositions were developed with novel screening procedures using for the first time fixed cells, cell lines. Also cell organelles interact with various alkyl-acyl-lipids originating from AAGPC. A quantified extract was used here for the first time obtained from whole blood namely "biological paf" which is a mixture of all alkyl ligands competing with Ginkgoloides for the same binding sites. Thus, Ginkgoloides are further selected in a novel manner out of the group comprising analogous and homologous compounds as well as natural and/or synthetic derivatives and/or out of the group comprising the known paf antagonists (Hwang, J. Lipid med. 2, page 123-158, 1990). In addition, the Ginkgoloides are selected using novel methods out of the great group of natural antagonists including the ginkgolides with mixtures thereof/therewith, the ginkgolide derivatives, the synthetic ginkgolides, the *Ginkgo*-extracts (EGB761, EGB etc), the phospholipids including paf analogues, the synthetic substances out of the group comprising triazolames, brotizolames, thiodiazepines, the thioetherbenzodiazepines (e.g. BN 50739), the etherbenzozepines, the chlorophenylbenzo(dia)zepines or out of the group comprising tetrahydrofuranes, cyclopentanes and/or of the group comprising endogenous modulating compounds, the proteo-, peptide hormones etc.

The novel methods using fixed cells are also suitable to select novel Ginkgoloides, mixtures thereof/therewith, synthetic ginkgolides, *Ginkgo* extracts which are more suitable. EGB761 (EP 0312913) or EGB etc are further antioxidatively stabilized using selene, vitamin E wherein ethereal volatile oils are excluded by purification for the locally acting administration for the first time. The *Ginkgo*-compositions are not offered as pharmaceutical agents "forte . . . intense" because those agents have side effects which are not desired by healthy persons. Too high dosages of the components must be avoided leading e.g. to hypervitaminoses, hypercalcinosis (nephrolithiasis), bleeding problems.

2.2. Repairing Compositions and Deficiency Syndromes:

Amino acids and glucose solutions with antioxidatively stabilized lecithins, peptides, (phyto-) hormones, vitamins are suitable to repair/build up deficiency wherein free albumin can be added. Eating disorders, alcohol problems, disturbed alcohol catabolism, alkylacyl-like destabilisations ("AHA"-syndromes) lead to loss of appetite, malnutrition, deficient nutrition, intolerance of lipids and deficiency of albumin. Milk- or *Soja*-products were enriched with vitamins and/or amino acids, acetylcysteines to repair deficiency of albumin, acetyl CoA, minerals etc. for example against hepatorenal problems, dialysis, renal anemia. Milk is enriched here as repairing composition with vitamins out of the B group and also with fruits with benefit e.g. for seniors. Stem cells can be stimulated using erythropoeitin (peptide hormone) against severe renal anemia. All palliative compounds (mistel etc), analgetics are used for patients at the highest need, in palliative units.

2.3. Syndromes Related with Raised Body Weight:

The compositions of the invention contain prepared, semi-synthetic and/or purified compositions. These compositions adjust/complete healthy nutriments of own choice without claiming food and are offered as a whole in an entire form to the outside. The novel compositions above are further completed by iodide. Dietary fibers such as *Plantago ovata* or wheat cereals, and constituents, selenium are added to the compositions.

The compositions are adapted for persons with overweight and iodide is adjusted for example in the presence of critical thyroidea situation (thyroid gland enlargement, hypothyroidism, post-infectious thyroid problems etc) and/or critical lipid profiles. The undesired side effects of hormones e.g. of thyroid hormones are equilibrated in accordance with the invention. The "OMIH"-overweight-syndromes are treated using the compositions of the invention by preference in the presence of alcohol and/or nicotine consumption or after periods of deficiency or dietary periods whereby alkyl lipids increase. The alkyl-like destabilisation of cells is treated here wherein the symptoms, hematuria, diabetic risk and/or rise of blood pressure as early predictors for disturbed vascular smooth muscle cells and/or impaired glandular cells and also impairments in general of cells, tissue, organs. First, the decline of cells is indicated with albuminuria and/or rise of blood pressure as indicators and later those persons tended also to diabetes, impaired blood cells and decline of the skin, the bones, the brain etc. Albumin is endogenously consumed during "OMIH"-syndrome so that albumin and LDL synergistically damage with intermediate of AAGPC, its derivatives, products (e.g. acetylacylCoA) the cells in the entire organism including those of the skin, the subcutaneous-, adipose tissue, glands, neuronal cells and brain. The novel compositions healed with a surprising success.

2.4. Transposition of Hormones, Pharmaceutical Compounds:

The equilibration of hormones has been reached by preference by inhibition of AAGPC with products, derivatives in order to promote beauty, energy, wellness of mind and soul. An equilibration of the hormonal metabolism improves the critical lifestyle and vice versa. Ginkgoloides mediate for the first time also a hormonal equilibration and further promote the healing of early clinical impairments. Hormones are better tolerated and those are suitable to treat hormonal problems to meet e.g. borderline hypothyroidism, menopause/hormonal dysfunction, loss of energy, sleeping problems, loss of bone mass. It is known that peptide hormones such as thyroid hormones determine the expression of genes but an undesirable risk for diabetes with hematuria was observed here during treatment with thyroid hormones. Those were successfully treated by further reducing nicotine consumption. Hematuria, diabetic risk subsequently healed completely after several years of hematuria of a smoking women with overweight indicating an alkyl-related cell destabilisation of renal cells which was rather aggravated by hormones. A hypersensitivity syndrome of cells e.g. to hormones, lipids was not recognized up to now to be developed and treated here for the first time.

For pregnant women (and their children) who are at risk for intolerance to glucose, hyperinsulinemia, insulin resistance, weakening of children's health, adolescent obesity etc. by preference antioxidatively stabilized plant and fish oils are prepared which are rich in unsaturated and polyunsaturated fatty acids, lecithins, iodine, folic acid, selene, iodide, flavone glycosides, lecithins, vitamins, constituents and minerals. Milk-, vegetable-, fish products are recommended. Components are used here for the first time to purify endogenous albumin carried through the placenta barrier (using e.g. stabilized fatty acids, lecithins, selene). Light-related exercising is also recommended for pregnant women rather than paf antagonists to avoid disturbed regulation of uterine contraction. Iodide, hydrophilic folic acid are always added and are adapted for women of reproductive age who want to be pregnant and/or in cases of anemia and/or to promote the aging brain, or against hypothyroidism or against homocysteines. The known successful strategy for health promotion is described with a follow-up of pregnant women in the priority document (P34669914).

Hydrophilic ginkgolides which were considered up to now as being inefficient and/or lipids, antioxidatively stabilized phospholipids, peptides, synthetic substances can replace the alkyl glycerol, alkyl LPA, lyso paf in/on albumin while lipophilic ginkgolides and iodide show here benefit in/on cells, brain, lipoproteins. Iodide equilibrates the thyroidea gland and lowers blood lipids.

The compositions of the invention comprising Ginkgoloides and/or acetylcysteines are supplementary and equilibrate all hormones and antagonize hypersensitivity syndromes also during intake of the classical hormone replacement therapy. The Ginkgoloides antagonize an undesired proliferative effect of hormones and/or acetylcysteine makes hormones less potent by intermediate of acetylation. Alkyl lipids, alkyl-like lipids and acyl groups accumulate in cells in the presence of critical lifestyle wherein alkyl-acyl-GPC (AAGPC) destabilize the cells in the alkyl-liCe manner with intermediate of derivatives. The means that alkyl lipids and products, namely acetylacylCoA impair e.g. the (re-) synthesis of acetylcholine out of choline and acetyl CoA. Acetylating compounds antagonize here for the first time the hypersensitive imbalance and prevent activation, differentiation (apoptosis), exhaustion (degeneration) of cells. The exhausted glandular and neuronal tissue show similar fatigue effects and accumulate undesired endogenous compounds. Alkyl-acyl GPC with derivatives, products destabilize the cells becoming then too sensitive to hormones. Hormones, phytohormones, prehormones are administered here in a more careful manner with precise, lower dosage and are adjusted with constituents, minerals or amino acids in accordance with the invention. Acetylcysteine provides substrate as e.g. pigment-promoting peptide hormones are lowered by acetylation and Acetyl CoA is ready for acetylcholine (re-) synthesis. Acetylcysteines and/or selene are further suitable against inflammations, tendency to infections. Promotion of the young brain is reached with compositions and/or adjusting genetic problems are reached with adapted and enriched compositions using by preference acetylcysteines and/or iodide, selene (e.g. in the presence of trisomy, isoforms of lipoproteins, acetylhydrolases, alcohol reductases, connexines etc).

The compositions with Ginkgoloides causatively antagonize the mental, neuronal, cerebral, episodic cardiac, cerebral epileptic impairments e.g. of the brain or of the heart and show an analgetic benefit. The side effects of hormones, medicaments are reduced by the composition. Drugs, peptide hormones such as thyroid-parat-hormones, cholestan derivatives, antiepileptic drugs or marcumar etc. trigger the loss of bone mass while the compositions equilibrate in a determinating manner.

2.5. Skin

The skin problems begin early and indicate the alkyl-related impairment of cells wherein also the dietary compositions protect against skin wrinkles and strengthen the endogenous sun protection system. Sun screening agents and ginkgoloides are combined here for the first time with all known locally caring application forms. Locally acting preparations are composed with free albumin, antioxidatively stabilized lecithins, ceramides, unsaturated fatty acids, plant and honey products and are suitable to take care of the skin, the connective tissue. The novel composition is required in the presence of eating problems, weight problems, hormonal problems, hormonal transposition periods, malnutrition, uptake of hormones and/or during aging. The benefit is shown with entire healing of disturbed connective tissue (striae) and/or impaired pigmentations by preference vitiligo, age-related pigmentations, chloasmen, melasmen, melanosis, light-sensitive dermatosis using percutanous applications and/or by modulation of the (central) hormones. A cosmetic, dietary, protective composition against impaired pigmentation comprising Ginkgoloid is directed against alkyl-acyl-GPC with derivatives, products and at least one sun screening agent or an acetylating substance is used to protect similar cells of the skin, skin-connective tissue and the nervous tissue in a locally acting and centrally acting manner. A combination of specific and non-specific antagonists further protects against alkyl-lipids.

The compositions of the invention are novel and surprisingly fresh, as Ginkgoloides are combined for the first time with constituents and light-dependent prehormones whereby lecithins and/or Ginkgoloides are composed with sun screening agents.

3) THE UNEXPECTED CLINICAL PROBLEMS AND PATHOPHYSIOLOGY

Up to now the surprising problem of tie invention could not be recognized and was not obvious. The priority document (P 34669914) allows for the first time to see the unexpected clinical risk constellations including follow-up studies so that the novel compositions can antagonize for the first time these previously unrecognized problems, namely the critical lifestyle with (1) nicotine consumption (2) hypersensitivity against hormones, lipids and (3) hematuria, tendency to diabetes and/or (4) alcohol problems as those are significantly associated with defects (5). That means early kidney problems, albuminuria, hematuria, proteinuria, (6) hypersensitive vascular smooth muscle cells, rise of blood pressure and/or albuminuria with (7) loss of calcium as onset of loss of bone mass, tooth decay and (8) the disturbed relationship between albumin and lipids. Altogether the damaging transport of albumin from inside the vessels out is indicated and related with defects of tissue and skin (alb/trig). This is the borderline, named "OMIH" syndromes. The early defects include also weight problems of reproductive-aged women (e.g. aged 36±14 years) and significant gender differences. The hormonal, dietary, protective compositions reach then benefit with (10) unexpected equilibration of mental, affective, sensitive problems. A better quality of lifestyle, namely (11) reduced risk factors showed here benefit in the presence of problems related with weight, energy, beauty, nutrition, alcohol, nicotine and led to (12) an unexpected clinical healing.

The long term clinical follow-up studies (Bayerische Landesärztekammer, Ethik-Commission Nr. 02088) showed a surprisingly early prediction system. The fatty, alkyl-like destabilization of cells was recognized for the first time using "OMIH"-cells. This is a problem of the entire organism wherein even kidney defects, risk for diabetes healed after uptake of the inventive compositions. It was necessary to reduce the uptake of causal noxious compounds because the stable alkyl-lipids are formed in peroxysomes from fatty alcohols. In addition, nicotine mediates an alkyl-like effect by intermediate of lipid oxidation. Thus, the cells destabilize and become too sensitive in response to alcohol, nicotine wherein this risk combination decides. AAGPC and its derivatives (alkyl-lipids), products (acetylacyl CoA) accumulate inside of the cells and transpose the energy sources of cells by forming e.g. mevalonates that means more precursors of cholesterol are formed inside of all cells, cellular organelles, in the cytosol, endoplasmatic reticulum, in the nucleus (DNA) etc. resulting in a fatty cell degeneration. The compositions of the invention inhibit the formation of alkyl-acyl-products. The "OMIH" syndrome is a borderline syndrome with alkyl-acyl-like cell destabilization of cells and mental desequilibration. These cells are then too sensitive in response to the group of hormones as these differentiation agents (hormones, lipids etc) exhaust renal cells explaining then hematuria. The glandular cells are tired out predicting the risk for diabetes. The disturbed skin cells explain impaired pigmentation. Clinical benefit was shown against rise of blood pressure, prediabetes, albuminuria, hematuria, proteinuria ("OMIH"-syndrome). For example, persons with alcohol problems showed here raised blood pressure which was lowered from 145±22/89±13 mmHg to 123±12/82±10 mmHg. Those persons also showed early albuminuria (≥20 mg/l) which was lowered then from 50% to 20% in unpublished data with the first higher-risk subgroup (ABA, n=5, ±1 S.D.).

The compositions protect the whole organism in a long lasting manner using low dosages to reduce the now predictable risk and damages that means decline of vascular, neurovascular, cerebral functions wherein alcohol and nicotine are reduced. The compositions predict and antagonize now degenerative, cerebral suffering earlier. For example, the risk for stroke can be recognized prior to irreversible impairments and those are detectable. For example, an efficient use protects the organs, brain and vascular perfusion and an efficient cerebral use protects against seizure disorders, headache, cramps, epilepsia. The nonsteroidal antirheumatic drugs are replaced here as far as possible by the compositions as hypertension, bleeding problems and impaired cognitive functions increase under nonsteroidal drugs.

Rise of blood pressure and prediabetes clinically indicate the unexpected defects of differentiated cells such as smooth muscle cells of small vessel (arterioles, capillaries, venoles) or of the insulin-forming glandular cells in the pancreas. Prediabetes and hematuria are healed on a sustained basis for the first time wherein the compositions comprising hormones, Ginkgoloides and at least one mineral, one constituent protect also large vessels whose intima are protected by nutritional vasi vasorum.

The transport of albumin and calcium into the tissue is antagonized in an integrating manner to early protect all tissues including the brain against the damaging ligands of albumin. Venous and lymphatic vessels are further strengthened so that the emigration of disturbing albumin-ligands is reduced. Only free (pure) albumin can protect incorporating alkyl ligands but only low amount of free albumin is still present during "OMIH"-syndromes. Albuminuria with rise of blood pressure shows the risk which is aggravated by LDL and critical lifestyle with intermediate of alkyl, alkyl-like lipids. The significant and early rise of blood pressure is improved by the inventive composition. The energy balance was equilibrated (mitochondrions, peroxysomes, smooth muscle cells) and neurovascular regulation (endothelial pericytes, smooth muscles) cared, equilibrated wherein the long lasting successful therapy supports the hormonal, genetic, regenerating transposition.

Skilled persons recognized the "OMIH" syndrome as independent syndrome while the early begin of damages in the presence of borderline syndromes caused much surprise ("so early!!"). These unexpected borderline syndromes were characterized by "overweight, mixed hyperlipidemia and/or intolerance to glucose (borderline) hypertension and critical morning urine samples. A particularly harmful effect was mediated in the presence of raised LA-paf in/on LDL in the presence of nicotine- and alcohol consumption which was then significantly associated with rise of blood pressure, diabetic risk and albuminuria (Table 2). Thus, the treatment is the onset of a healthy middle phase of life and not the sad end after manifest diabetes mellitus, hypertension, obesity that means of metabolic syndrome with secondary dementia etc. The immunological response, health, wellness, beauty, joy, equilibration, the psychological, intellectual health are promoted in an early adjusting manner using an integrating strategy including light and exercises. The repair of raised blood pressure, diabetic risk, hematuria and disturbed skin meets age ("happy aging").

The causative treatment neutralizes the decline of vascular, cardiac, neurovascular functions, (secondary) dementia, decline of tissue, organs, problems of aging, beauty, immunology, metabolism. An endocrinological equilibration is reached including soul, intelligence, mentality, the brain. There is a protection against seizure disorders by preference against alcohol-related, cardiac, cerebral, psychological, intellectual, neuronal, mental problems, against pain attacks and/or against psychotic and/or paranoid phases. Even the severe alcohol-mediated damages of "Rosenkavalier" healed and/or the nicotine-mediated damages of "Saturn"

Another variant of the invention is the equilibration of side effects of hormones or drugs. Hormones protect against premature aging and have beneficial effects in view of critical lifestyle behavior but hormones further mediate loss of bone mass (parat-thyroid-steroid-hormones) and/or can trigger melanosis and causing then vascular degeneration and mental crises (depression, psychosis). Thus, the inventive composition has to causatively antagonize the hypersensitivity to hormones by preference among indicated persons at risk. In addition, the compositions reduce cognitive problems which are rather aggravated e.g. by psychopharmacological agents (e.g. by tricyclic antidepressive drugs).

Tested urinary albumin is used to recognize an early silent loss of calcium and this is antagonized when the calcium-phosphate metabolism is repaired. All cells are protected including cells of the bone, tooth against decline of muscle, nerves and/or organs. The loss of calcium and of bone mass and of tooth matrix is inhibited. The calcification of the arterial intima is often paralleled with loss of bone mass. The degenerative, calcium-, amyloid-dependent defects of neuronal cells are known and those are especially dramatic with/in the presence of pre-injured nervous cells. In addition, adipose tissue is reduced, purified here so that hypertensive inflammatory substances are also lowered (e.g. CRP etc.). Hypertension, diabetic risk and/or amyloid raised during chronic infections whilst the novel compositions are especially important also for aging persons, or for those with critical alimentation and/or at genetic risk or for persons who are risk for degenerative disorders and/or for those with hypersensitivity syndromes. The novel compositions bind calcium and phosphor to the bone mass. Hormones and Ginkgoloides equilibrate as well and acetylcysteines lower the potency of hormones and provide substrate for Acetyl-CoA. Altogether, this is the way to causatively protect the brain over a long time period.

The first morning urine samples with albuminuria, proteinuria, hematuria also indicate a risk for carcinogenesis as well as genetic, neoplastic impairments or late renal urological problems which are antagonized in time. Nephropatic, neoplastic and carcinogenetic problems are treatable and early diagnostic methods are improved based on first morning urine samples (proteinuria, hematuria, albuminuria, protein profiles, urine microscopy, antibodies, proteomics, clinical chemistry, genes, genetic mapping etc.).

For younger persons at risk lower dosages are by preference suitable to protect the young brain. Lower doses promote the brain during the early childhood as well especially in the presence of a genetic risk-profile. Quite surprisingly, acetylcysteine is used here and repairs then acetyl-CoA e.g. in the presence of genetic isoforms of acetylhydrolases. Acetylcysteines antagonize inflammations and promote the infant brain e.g. during pregnancy. Those inventive compositions complete here a healthy nutrition e.g. in the presence of inflammatory gastrointestinal disorders and/or loss of appetite after/during deficiency, need (compositions adapted for medical use).

Especially women have a great need of health-promoting compositions comprising light-dependent hormones against loss of bone mass. Thus, the novel compositions are developed for an integrated gender concept regarding by preference the differences of men and women. Novel methods of manufacturing are specified (in P3466914) and are included here by citation for the locally acting compositions comprising hormones. Men more often report here alcohol problems and react more sensitive with rise of systolic, diastolic blood pressure and lowering of HDL. Women rather tend to have overweight with critical LDL-levels. These women often smoke against overweight and/or to repair psychological, social, mental problems. Men and women with critical lifestyle, alcohol, nicotine, weight problems show significantly declined ratio of albumin to triglycerides "alb/trig" wherein the disturbed relationship was repaired with the inventive composition. The plasmatic, extravascular, cellular carriers (alb/trig etc) were purified and the hormonal metabolism was normalized. The compositions of the invention improve the lifestyle and then overweight, mixed hyperlipidemia, rise of blood pressure. The hypersensitive vascular smooth muscle cells of arterioles, venoles can recreate. Intolerance to glucose with albuminuria, proteinuria, hematuria was called "OMIH"-syndrome and was healed.

The compositions of the invention protect here in an integrated manner by preference all cells of the entire organism and penetrate cartilage, bones, muscles, tissues, sinews with cleaner free albumin. Also persons at risk are protected by preference women, adolescents, persons with addictive problems and/or aging, invalid persons and/or persons with problems concerning body weight, metabolism, alcohol and/or nicotine ("AHA" syndromes, "OMIH"-syndrome), as there was a healing of early and late impairments. Beneficial effects were found based on the constitution of body and soul and further improves the lifestyle as well.

4) PROBLEMS OF SKIN AND BEAUTY

Novel compositions are developed for the skin to protect skin cell (ceratinocytes and melanocytes) by preference against pigmentation problems. An accumulation of alkyl lipids (AAGPC/LA-paf) in the entire organism mediate impaired pigmentation of the skin to be antagonized by sun screening agents. Cleaner compositions for topical administration without ethereal volatile oils are used by preference in the presence of critical lifestyle, higher age and/or critical hormonal transposition periods, during pregnancy etc. The sun protection of the skin is strengthened by psychological, intellectual, mental recreation leading to better lifestyle as well reducing then problems of body weight, addiction and declined tissue. Those problems led to the preparation of a risk-related cosmetic strategy using the dietary and/or locally acting compositions of the invention. The unexpected pigmentation problems of the skin were mediated by ethereal volatile oils led to the inventive composition's with Ginkgoloides and sun screening agents.

The locally acting and dietary compositions are convenient to each other. Light-dependent hormones, prehormones are suitable in the presence of intensive sun protection by externa or clothing. On the other hand sun protection is desirable. Light-dependent hormones must be supplemented at exceptional risk, namely of women, malnutrition, culture barriers, enhanced need, aging, genetic risk, untidy lifestyle and/or in the presence of extremely intensive sun protection. The potency of the melanotropic hormones of the pituitary gland is lowered by acetylation.

Sun screening agents are added to the locally acting composition in accordance with the invention when locally applicated compounds with Ginkgoloides are prepared for skin care. Appropriate local compositions comprise sun-screening agents, Ginkgoloides, lecithins and ceramides stabilized with antioxidants protect the skin by preference against pigmentation problems e.g. mediated by ethereal volatile oils. The compositions of the invention are suitable for oral and/or for cosmetic applications, adjust hormones and strengthen the cells of the entire organism including those of the skin, scalp, adipose tissue, brain, organs, overall of the tissue.

5) THE GALENIC PREPARATIONS

The compositions of the invention are manufactured using isolated, prepared and/or (semi-) synthetic components worked up to efficient compositions. All components are stabilized with antioxidants and adapted regarding the before mentioned risk profiles. Analogous, homologous, synthetic derivatives of the components and those are products, for example from plants, animals, micro-organisms, fungal products and products from cell lines and bacterials.

The galenic preparations are included by citation of P34669914. The oral and/or local, percutaneous administrations are used by preference while subcutaneous, intramuscular, transdermal, intravenous, trans-, intranasal, rectal, inhalation forms of administrations are possible etc. Tablets, coated pills, capsules, elixirs, liquids/solutions, suspensions, gases, syrups etc can be manufactured with all appropriate non-toxique adjuvant agents.

For example, antioxidatively stabilized compositions are mixed here using a sterile container, indicated by a list of ingredients. The date of manufacturing, expiry date (about 6 months) are indicated as well. The ingredients are offered in an united form to the outside and the container, are indicated by a trademark of the applicant. The container is placed into a second container and is given away in the inner side with the second light-protected container. The composition adjusts here, for example low fat milk (1:9, vol/vol) without claiming this milk.

5.1. Adjusting Compounds:

The compositions of the invention cause hormonal effects and adjust hormones with nutrition components, pharmaceutical compounds. Thyroid hormones are commercially available wherein iodide is enriched here for the first time in the compositions of the invention. The hormone replacement therapy is commercially available and offered as combined (combi) package (kits) for oral-dermal, vaginal, rectal administration wherein the compositions of the invention are composed here for the first time together with (phyto-) hormones. There are commercially available combined packages comprising drugs against/in the presence of loss of bone mass (e.g. biphosphonates) for two-stage administration of vitamin D and calcium wherein the composition of the invention is manufactured here for the first time with Ginkgoloides, constituents, prehormones. The calcium-complexes are prepared as classical preparations for sherbet liquids also with Ginkgoloides.

The compositions operate synergistically with antihypertensive drugs for example with Betablockers and aldosterone antagonists, so that combi packages (kit) are suitable (e.g. also with angiotensine antagonists) or with diuretics as shown during the onset of the treatment. Combined packages are by preference suitable to complete lipid lowering compounds (e.g. statins, fibrates, benzodiazepines etc) and/ or all antidiabetic compounds (e.g. Cannaboid receptor antagonists, insulin sensitizer). Combined packages/container (kits) are suitable to administer the compositions using a simultaneous or two stage use for local percuateneous and/or oral administration, are given away in united form to the outside. In addition, persons at risk can adapt their combined packages for their need regarding their elected nutrition, their deficiency of light, of exercising, their life crisis and their beauty problems. Combinations are more suitable here compared to highly concentrated drugs such as "special *Ginkgo* extracts . . . forte intens" because the persons in need are at higher risk for bleeding (e.g. hypertensive persons or those with liver cirrhosis, nephrosis).

5.2. Novel Methods of Manufacturing:

In accordance with the invention, cleaner active ingredients are prepared here for the first time using oily preparations, which are antioxidatively stabilized and purified in an appropriate manner. Lipophilic properties are used for the first time. The novel methods of manufacturing and screening are included here by citation of the priority document (P 34669914). For example, the lipophilic t-butyl groups determine the efficiency of ginkgolides and thus of *Ginkgo biloba* extracts so that trilactones comprising only one butyl group (bilobalide etc) cannot be considered here as being a Ginkgoloide. Each additional polar group or even the opening of only one of the lactone rings dramatically impairs the efficiency (R. Korth, Eur. J. Pharmacol. 152, S. 101, 1988). The peripheral cells are by preference protected against alkyl lipids using peripheral benzodiazepines as those share the appropriate pharmacological regression lines.

The antioxidatively stabilized, enriched carrier oils are administered with light-protected ampoules (2-10 ml) or with capsules (e.g. 1-2 ml). The material of the capsules allows therewith release in form of retardation, nanotechnological, two-stage or continuous release of the compositions and/or components. Adjusted, light-protected plant oils (e.g. pumpkin kernel oil, olive oil, *Soja*) are mixed with antioxidatively stabilized fish oils which are further enriched with Ginkgoloides, dietary fibers, iodide without problems e.g. against overweight. Plant oils and fish oils are selected, elected and stabilized in view of most favorable ingredients. These ingredients comprise amino acids, peptides, phytohormones, hormones, prehormones, chinones, enzymes (e.g. biotine), proteins, peptides, sterines (sterols), minerals, e.g. calcium, phosphor, magnesium and vitamin A,B,C,E,K, iodide, selene in a diluted form. Lecithins and unsaturated fatty acids are further antioxidatively stabilized (selene, vitamin E), so that an excess of antioxidative compounds is present. These oils incorporate lipophilic and hydrophilic Ginkgoloides without further problems of taste or of solvents.

The dietary preparations are by preference oily compositions containing phospholipids which can solubilize/dilute polar and nonpolar substances as known (see lipoproteins), while the phospholipids must be further antioxidatively stabilized in order to avoid headaches, attacks (such as migraine, epilepsia, arrythmias etc). Lipophilic components penetrate membranes and accumulate in cells, cell compartments, tissues, in the brain with cellular and central effects. Ginkgoloides can be selected out of specific, antioxidatively stabilized lecithins using novel methods which are suitable as non-specific alkyl antagonists and those include a great group of hydrophilic and/or lipophilic, synthetic, semi-synthetic substances. The additional antioxidative stabilisation is important because the oily carriers are used to increase efficient elevated levels of the compounds in the entire organism also in the brain. Novel oily compositions are clinically developed using non-specific and specific alkyl antagonists. These antagonists healed and regenerated then in a representative manner without side effects.

5.3. Preparations of Sherbet Liquids:

By preference the combination with acetylcysteines and/or calciumcarbonate, calcium citrate is suitable for preparations of sherbet liquids. Classical methods are preferred here as ginkgolides are not weakened by moderate changes of the pH values contrary to statements of third parties which might be guided by profits. Compositions suitable for sherbet liquids (powder, granules, tablets) are diluted with water just before intake to be subsequently taken without problems. The compositions of the invention contain stable Ginkgoloides and are furthermore carefully antioxidatively stabilized (e.g. with selene, vitamin E). The loss of instable trilaktones, namely of bilobalid is expressively desired here (Oschmann DE 19509856, filed Mar. 17, 1995). The free classical methods used for manufacturing preparations for sherbet liquids since decades using e.g acetylcysteines and/or calcium are suitable for the compositions of the invention using the "preparation of ginkgolides as mixture" (R. M. Korth EP 0312913; Schmidt et al., Die Pharmazie, February 1990, vol. 45, p. 89-101).

5.4. Protective Products:

The locally acting preparations are manufactured without ethereal volatile oils or perfumes to avoid pigmentation problems. Ethereal volatile oils are cleaned out and more pure substances are then composed. Furthermore, lecithins, ceramides, unsaturated fatty acids are particularly stabilized with antioxidants and are used then for the locally acting preparations of the invention. Gingkoloides are administered with these high quality carriers further comprising sun screening agents and these preparations are offered in a united outer form.

The local, percutaneous, cosmetic compositions of the invention are administered in a simultaneous, multi-timed, locally acting and/or as oral form e.g. using combination packages. Cures/recreation packages, enriched compounds for the skin, scalp, teeth, plasters, gels, emoliant/creme-lotions are suitable and all commonly employed galenic preparations.

In the presence of disturbed connective tissue e.g. oleaginous substances are massaged in and those subsequently get a more efficient long term outcome using a second more fatty creme e.g. during pregnancy or overweight as representative problems related with hormones, alcohol, aging. The plasters and gels etc. reach similar long term effects.

In the presence of beauty and/or connective tissue problems, packages, cover materials, masks promote the cosmetic effects forming intertriginous zones as explained before. Fatty preparations increase the penetration into deeper skin regions using by preference dual-timed physical applications with perfusion effects and by supporting the connective tissue (hot and cold showers etc).

Against scalp problems overnight cures/treatment are suitable comprising *Ginkgo*-, oils, hormones, vitamins especially of the A,B,C-groups, Siliceous Earth or wheat germ with selene better penetrate the skin using massages. These cures protect against hormonal scalp problems using natural, synthetic, semi-synthetic hormones and antagonize, for example the bald forehead of women together with the inventive compositions for oral use, for example as combined packages. The scalp is purified in the morning by preference with products comprising lecithin which can contain also Ginkgoloides. This recreation treatment shows benefit against pruritus and scales also of men.

Cooled gels especially show benefit against dermatological skin and/or scalp problems by preference in the presence of pruritus and/or high fat compositions comprise Ginkgoloides with vitamins of the B group. The gels penetrate overnight in a two-stage manner and are massaged in. The skin is equilibrated, anti-inflammatory effects protect and perfusion is promoted therewith. Children and adults are carefully treated suffering of neurodermitis, sunburn, insect stings etc. repairing then the painful irritations.

5.5.1. Liposomes:

Liposomes are by preference suitable (e.g. R. Korth, EP 0648 488, 1994) for the compositions in accordance with the invention. Ginkgoloides, prehormones, hormones, minerals and constituents are taken up in an equal manner using liposomes and can e.g. simultaneously work inside of cells. Liposomes carry components with different solubility including the hydrophilic folic acid. Difficult localization of active sites are reached for an intra-, extracerebral, intradermal, percutaneous, extradermal, simultaneous and/or multi-timed effect in the perfused and penetrated tissues reaching then a protective purifying outcome regarding also lipids, peptides, proteins, lipoproteins etc.

Liposomes are a galenic form and are free state of the art so that prepublished mixtures and administrations can be adjusted here in accordance with the invention so that the compositions are novel and unexpected. The compositions of the invention for skin care or scalp care protect for the first time using Ginkgoloides together with sun screening agents in a simultaneous or two-stage use including all known galenic preparations, also liposomes. In addition, antioxidatively stabilized lecithins are desired as non-specific alkyl-antagonists and antioxidatively stabilized long-chain ceramide care (e.g. out of *Soja*). Removing ethereal volatile oils is very important to avoid pigmentation problems which are aggravated by hormones, alkyl lipids and/or ethereal volatile oils and/or by the harmful non-specific uptake of alkyl lipids (impairments of pigmentation, vitiligo, melanosis etc.). The adjusting oral compositions inhibit the central melanotropic peptide hormones e.g. by acetylation.

5.5.2 Compounds Against Impairments of Pigmentation:

Stabilized cosmetic carriers are worked up to reach high quality without ethereal volatile oils, perfumes and those carriers are selected. Galenic preparations are adapted to the specific character of the skin, the target and/or the hormone type. An unexpected pigment-disturbing effect was recognized for example with special *Ginkgo biloba* extracts (EGB, EGB761) with testified self-treatment wherein the novel compositions repaired those pigmentation problems. The priority document (P 34669914) reveals for the first time the combination of Ginkgoloides with sun-screening agents in a united outer form. The carrier oils, Ginkgoloides and/or *Ginkgo* extracts are made free from ethereal volatile oils for the first time.

Special *Ginkgo* extracts "forte . . . intense etc." which mediated the pigmentation problems were avoided. Food products, herbal mixtures, general purpose therapy for inside and outside of the body are not suitable for/against the novel hypersensitivity syndromes. Symptomatic therapeutic approaches are left behind using "forte . . . intense, for internal and external applications without precise effective mechanisms compared with the unexpected, precise and holistic therapeutical methods of the present invention.

Lower dosages (diluted), high quality, cleaner components are offered here as united outer form to equilibrate the hypersensitivity syndromes with benefit on skin tissue and the hormone turnover. Lipophilic and hydrophilic, specific and non-specific antagonists neutralize here the long term damages mediated by alkyl lipids in the whole organism in an efficient manner for the first time.

6) UNEXPECTED PATHOMECHANISMS AND NOVEL METHODS

The FIG. 1 shows the composition of the invention, which was developed to antagonize the unexpected risk profiles. The compositions are identified with the trademark FIDA®. The composition comprises 3 ml pumpkin kernel oil, 1 ml folic acid, 2 ml fish oil with vitamin E as stabilizing antioxidant and 3 ml diluted gingkolides. The composition of the invention supplements food products (2 ml per day) and is used here for example with lipid-poor milk (unclaimed).

The following experiments show that alkyl-acyl-GPC is accumulated and alkyl-acyl-choline groups lead then to an allosteric effect. The alkylacyl-like destabilisations were not mediated by apoproteins (ApoB) and not by cholesterol and/or triglycerides (VLDL) while this is an allosteric alkyl-related effect as shown here with fixed cells. The methods are extensively specified for the first time (in P346609914) and included here by citation.

6.1. Fatty Alkyl-Related Cellular Destabilisation of Differentiated Cells:

The accumulation of AAGPC is invented here wherein AAGPC and derivatives are inhibited by Ginkgoloides and free albumin. Human platelets are examined and treated as model for differentiated cells e.g. nerve cells, cells of the heart, skin, bone, smooth, striated muscles, organs, glands such as beta cells of the pancreas, those of the pituitary gland etc. The cells in the presence of the "OMIH"-syndrome were in vivo determined in a negative manner as those bind more alkyl lipids and form more alkyl-acyl-GPC with derivatives, products. Cells, cell organelles (peroxysomes, mitochondrions, DNA) are destabilized and said compositions healed here the clinical impairments in accordance with the invention.

The FIG. 2 shows an increased non-specific binding of alkyl lipids (such as [$^3$H]alkyl-paf) to washed aspirinated platelets in the presence of "OMIH"-syndrome (A). These washed aspirinated "OMIH" cells bind more [$^3$H]alkyl-paf compared to normolipidemic platelets (B) which do nearly not incorporate [$^3$H]alkyl-lyso paf and thus do not form AAGPC and LA-paf (C). These women with "OMIH"-syndrome show overweight (aged 34±11 years, BMI: 25±5 kg/e), raised LDL (167±15 mg/dl, HDL: 76±41 mg/dl) and triglyceride levels (206±27 mg/dl) borderline hypertension (125±13/88±10 mmHg) and disturbed glucose tolerance (1 h: 170±61 mg/dl). Three of these four women drank alcohol and two of those showed hematuria and/or proteinuria.

Ginkgoloides with free albumin (BSA) inhibited here the binding of [$^3$H]alkyl-paf to "OMIH"-platelets after three washes (FIG. 2 A+B). The high non-specific binding showed the alkyl-related binding of [$^3$H]alkyl-paf thus the alkyl-mediated determination (A), which is also supported by the following shown allosteric alkyl effects. Normolipidemic platelets do nearly not incorporate [$^3$H]alkyl-paf or [$^3$H]alkyl-lyso paf and form nearly no AAGPC and LA-paf in the presence of Ginkgoloides and free albumin (FIG. 2C).

The FIG. 3 shows the mechanism of the AAGPC production wherein LA-paf in/on LDL makes differentiated cells ready to incorporate alkyl lipids (FIG. 3E versus 3A-C). Only LDL but not ApoB and not VLDL overcome the protection by albumin (FIG. 3E versus 3D). ApoB or VLDL form lyso paf without cellular uptake (FIG. 3 C+D) while free delipidated albumin or HDL incorporate [$^3$H]alkyl-paf which then remains stable with or without cells. In the presence (A+C) or absence (B) of washed platelets nearly no AAGPC with derivatives and products is formed. The acetylhydrolases form lyso paf and LDL, of apoB and VLDL also form lyso paf whereby the uptake of lyso paf is triggered by LDL.

The FIGS. 2 and 3 enclose the clear therapeutic instruction to lower the damaging AAGPC with its derivatives and products (FIG. 2 A-C, FIG. 3C+F) in order to antagonize the LDL-mediated scavenger condition of cells. Otherwise, alkyl-acyl-sn-glycero-3-phophocholines (AAGPC) accumulate in cells and is substrate for lipases, hydrolases, transferases etc as known. Following formation, release of alkyl-glycerols, alkyl-phosphoglyceroles (LPA), alkyl-phospholipids, alkyl-ethanolamines, alkyl-lipids, alkyl-cannaboides are also known. Also acyl products of AAGPC are inhibited here in accordance with the invention to antagonize the novel hypersensitivity syndromes.

6.2. Fatty Alkyl-Like Cellular Destabilization of Non-Differentiated Cells:

The FIG. 4 shows the saturated unspecific uptake of alkyl lipids by non-differentiated cells. The non-differentiated washed blood leukocytes incorporate here [$^3$H]alkyl-paf with intermediate of [$^3$H]alkyl-lyso paf and form alkyl lipids (AAGPC+LA paf) in a saturated manner (A: 0.65 nM vs. B: 6.5 nM) wherein unlabelled paf fails to replace (B, 5 nM). Thus, at least one non-specific transport protein is indicated (e.g. acetylhydrolase) on undifferentiated cells. The less differentiated cells are invented here as a model for monocytes, endothelial cells, glia cells, cartilage cells, adipocytes, endogenous stem cells etc. The acetylhydrolases on plasma membranes of leukocytes remove alkyl lipids and these cells are then pre-activated, differentiated and ready to emigrate. Non-specific antagonists e.g. free albumin protect against alkyl ligands and compete with cells for binding of alkyl lipids. The fatty decline of cells in the entire organisms is clinically healed here. A lower amount of AAGPC is formed in the presence of Ginkgoloides and free albumin causatively antagonize the fatty alkylacyl-related destabilization of cells in accordance with the invention and with experiments.

6.3. Binding of Alkyl-Lipids to Fixed Cells:

The FIG. 5 shows that fixed platelets bind [$^3$H]alkyl-paf at 20° C. The FIGS. 6 and 7 show that Ginkgoloides inhibit in a concentration dependent manner the binding of [$^3$H]alkyl-paf to fixed platelets wherein the classical representative guiding substances are used namely BN 52021 as example for the original "chemically defined extracts of *Ginkgo biloba*" and WEB 2086 for known chlorophenyl-benzo(dia)zepines.

The FIG. 5 shows that fixed platelets bind labeled alkyl lipids only at 20° C. but not at 4° C. (FIG. 5D versus 5C). The allosteric alkyl effects are inhibited by stiffening of the membrane so that the scavenger-like allosteric configuration change of cells is shown as mentioned before. In contrast, the [³H]acetyl group of paf binds at 4° C. to fixed cells treated prior to the last wash with formaldehyde to be subsequently cooled and stiffened (1%, 30 min, A+B). The acetyl group binds and covers paf receptors without allosteric upregulation so that acetylating compounds are using this effect in accordance with the invention.

The FIG. 6 shows the screening procedure selecting Ginkgoloides, using fixed cells, fixed cell lines, testing BN 52021 as guiding compound, showing a dose-dependent inhibition of [³H]alkyl-paf binding.

The FIG. 7 shows for the first time the binding to fixed platelets of a non-separated alkyl ligand mixture extracted out of the whole blood ("biological paf"). An extract of whole blood, namely "biological paf" replaces [³H]alkyl-paf out of the binding and bind to similar alkyl receptors. This competitive inhibition is paralleled with similar effects of synthetic paf and with Ginkgoloides wherein WEB 2086 is used here as the known guiding substance for chlorobenzo (dia)zepines.

"Biological paf" is used here for the first time as non-separated ethanol extract of whole blood (without HPLC). This dry extract is diluted before it is quantified using aggregation of rabbit platelets in the presence of aspirin and CP/CPK. The novel methods allow for the first time testings without albumin so that alkyl ligands with lower cell affinity compared to albumin can bind in a detectable manner. For example, alkyl lipids without the choline group (alkyl-LPA) bind otherwise in deeper regions of the membranes of untreated cells and/or are rapidly incorporated into free albumin. In addition, the method is independent from calcium so that also calcium-independent alkyl ligands can be inhibited here (e.g. lyso paf). The clinical success against alkyl ligands is thus supported and can be carried out by skilled persons.

The FIGS. 5 to 7 thus show the novel screening procedure solves a novel technical problem, namely the variety of damaging alkyl lipids. The quantification is easier using fixed cells as the difficult acetylation step of alkyl lipids is removed which is required for calcium dependent quantification methods. Using fixed cells, cell lines also labelled antibodies and/or soluble transport-binding proteins can be tested and produced.

7. CLINICAL EXAMPLES

The successful clinical administration of the novel compositions was described here for the first time.

Overweight; malnutrition with rise of blood pressure, diabetic risk, critical morning urine samples ("OMIH"-syndrome) were healed and also an alcohol-mediated hepatorenal syndrome was repaired ("AHA"-syndrome) wherein the long regeneration periods indicated a genetic regeneration.

7.1. Example 1:

The Table 1 shows the successful treatment of a patient "Rosenkavalier" wherein his alcohol syndrome was initially defined elsewhere ("AHA"-syndrome) and was healed here 2002/2004. Next, he came into a phase as characterized by the "OMIH"-syndrome. Nephrosis, albumin levels, thrombocytosis, risk of bleeding (esophageal varices) had been successfully treated 2003/2004 (Quick 100%). Hypertension was further treated with Betablockers while diuretics were then withdrawn. First, full milk was given to him enriched with vitamins of the B-group, oats and fruits (namely iron in strawberries and raspberries) representative for patients at highest need (e.g. hospice, dialysis).

Since 2002 the before mentioned composition of the invention were gifted to the "Rosenkavalier" (FIDA®, FIG. 1) to antagonize also his unexpected "OMIH"-syndrome in the years 2005/2006 which was successfully treated here in accordance with the invention. Overweight remained but the mixed hyperlipidemia was repaired by the composition (Table 1). Lipid lowering drugs were not administered regarding the liver cirrhosis and also regarding his good lipoprotein isoforms (apo E alleles 3/3, no allele E4). The plasma albumin-level recovered preventing that he'll come into the phase of the dangerous encephalopathy (secondary dementia). A psychological, mental equilibration was reached using the inventive compositions which is documented here by five years of abstinence after alcohol withdrawal without help of third parties as confirmed by indicated laboratory values (Table 1).

Hematuria and albuminuria showed long term healing, repaired by the treatment. The renal loss of calcium decreased from 38 mg/l to 18 mg/l per liter of urine and lyso paf decreased from 52 pg/l to 25 pg/l in parallel with repaired declined albumin. These calculated data show the calcium-repairing and cell-protecting benefit of the inventive compositions, wherein it was possible to successfully treat the "OMIH"-syndrome in the years 2005/2006 (Table 1). The renal anemia remained and was repaired with erythropoeitin. The ultrasound of the abdomen was performed each year and confirmed liver cirrhosis without carcinogenesis. The carious remaining teeth could be treated but the "Rosenkavalier" began another life elsewhere in a catholic residence for homeless men.

The final testing of the first morning urine samples excluded then severe nephropathic disorders (e.g. on Oct. 28, 2005) while micro-albuminuria (22 mg/g creatinine <20) and also proteinuria (129 mg/g creatinine <120) remained confirming borderline vaues but then without hematuria and without pathological casts. The Table 1 shows normal blood pressure in the presence of the remaining basic treatment (Propanolol as Betablocker and Spironolactone as aldosterone antagonist). Blood pressure was tested 24 h elsewhere showing a normal nocturnal decrease so that the renal endothelial dysfunction was repaired. The vascular smooth muscle cells remained hypersensitive during the years 2005/2006 as blood pressure suddenly increased during stress or during periods without intake of the compositions (e.g. 180/100 mmHg). The unexpected "OMIH"-syndrome of the years 2005/2006 was healed as far as possible. A survival time of five years after an acute hepatorenal failure/insufficiency was a surprise for persons skilled in the biomedical field. The composition of the invention showed thus an unexpected healing.

Urological, nephrological, hepatic, neurovascular, vascular, neurological, neoplastic, cardiological, cellular disorders, stroke, bleeding, secundary vascular dementia, carcinogenesis, nephrosis, hepatic and/or renal encephalopathy and also the otherwise so typical broken bones and wound healing problems were prevented (subsequently to open legs). The heavy alkyl-related destabilisation of cells was repaired while some impairments remained for example the raised Gamma-GT, the renal anemia, the hypersensitive vascular smooth muscle cells. The microvasculare problems and also the addictive problems were repaired without help of third parties, as the "Rosenkavalier" remained abstinent and took the compositions of the invention. Administration of the composition reached the benefit of body, mind, spirit and mentality including benefit of the lifestyle and the entire organism.

7.2. Example 2:

The statistically significant "OMIH"-syndrome is characterized in the Table 2 including clear therapeutical instructions. The critical lifestyle with additive harmful effects must be improved with still healthy persons at risk. The Table 2 shows the significant associations between "OMIH-syndrome" with related overweight (BMI1+2) and raised blood pressure (RR) mixed hyperlipidemia (LDL-Trig, Trig) (p<0.05), LDL-related intolerance to glucose (LDL-IGTT) by preference in the presence of alcohol use (AHA, p=0.011) and/or nicotine problems. Alcohol consumption was associated with rise of body weight and microcirculatory injury (p<0.05). Hormones did not mediate direct impairments.

The Table 3 shows the follow-up. Abstinent obese women do not show renal problems (BMI2) but blood pressure raised so that Table 3 shows the hypertensive effect of the adipose tissue. The direct renal defect remains in the presence of alcohol misuse (ABA), but the blood pressure showed benefit in parallel with lowering of blood lipids. Women with overweight (BMI1) were older and more often smoked (57%) against overweight. The clinical follow-up studies are more extensively described in the priority document (P 34669914) and are included here by citation.

In the presence of critical morning urine samples by preference with alcohol and/or nicotine problems urological infections and/or carcinogenesis were excluded (sticks, protein profiles, urine microscopy, labeled proteins, lipids, alkyl lipids, matrix proteins, protemonics etc.). A diagnostic value of alkyl lipids is used e.g. against neoplastic cells, carcinogenesis for example urological, nephrological neoplastic disorders using also medical imaging (e.g. NMR, PET-Scan etc).

7.3. Example 3:

The Table 4 shows the time course of healing of hematuria and prediabetes as indicators of hormonal hypersensitivity. A case of hypothyroidism was continuously treated here with thyroxin and iodide while hematuria with diabetic risk remained. Hematuria and prediabetes showed a long term healing just after reaching an equilibration of psychology and mind, namely by better lifestyle with reduced nicotine consumption (from 20 to 6 cigarettes per day) because the alkyl-like cellular destabilisation was inhibited.

Overweight, rise of blood pressure, critical lipid profiles, albuminuria, proteinuria, hematuria, nicotine problems were treated in accordance with the invention including hormonal compositions. Beauty and vitality were promoted and the connective tissue was strengthened. Problems of mentality and psychology were solved in parallel with increased quality of lifestyle without help of third parties so that the hormonal therapy was well tolerated here.

8) THE PRE-PUBLISHED STATE OF THE ART

The research report of the German Patent Office dated Sep. 28, 2006 is based on the prior German application No. DE-102005062417 (filed Dec. 27, 2005, here P34669914). This research report objects the below mentioned valid US patents as summarized in the published patent applications No. US 2002/0127287 (publ. Sep. 12, 2002). Applicant's utility model DE 29700734 U1 and the foreign OS DE3929763 are also cited as objections.

None of the objections shows the hormonal compositions or render obvious the methods of use as claimed. The US Patent Office confirmed in the Office Action dated Jun. 19, 2003 that the published US Patent No. 2002/0127287 (publ. Sep. 9, 2002) is double claimed matter regarding the mother applications, namely U.S. Pat. Nos. 5,346,894, 5,605,927 and U.S. Pat. No. 5,852,052. In addition, valid U.S. Pat. Nos. 5,480,881 and 530,033 were cited as objections as the methods of the claimed use against LA-paf are shown and the matter is also included here by citation of EP 0459432. The cited U.S. Pat. No. 5,696,114 is also explained/included here by citation. Applicant's valid U.S. Pat. No. 5,895,785 is also included by citation. Applicant showed in time many mixtures and methods of use with the utility model 29700734 U1 (publ. Jun. 26, 97) for local and dietary use including the special *Ginkgo* extract EGB761 with food ingredients, milk products, unsaturated fatty acids and/or vitamins (without disclosure of hormones, minerals as constituents).

Applicant claimed before many methods of use for paf antagonists and/or ether phospholipid inhibitors against mental, cerebral disorders, impairments of the blood brain barriers, sclerotic skin problems, metabolic syndrome and addictive disorders using in time original methods, pathomechanisms by preference binding assays and turnover of ether-(alkyl-) phospholipids by preference lyso paf and/or LA-paf. The original mixtures of paf antagonists were shown and claimed before in time (Ginkgoloides etc) for example triazolothienodiazepines, ginkgolides, Ginkgoloides with or without fish oils, vitamins, antioxidant compounds, steroids, cAMP-modulators, albumin, prostaglandin antagonists including oral, dietary, local, cosmetic administrations liposomes and also food, beauty products (Kits).

Next, valid European patent specifications are priority documents of the objections as discussed below. Paf antagonists are shown with garlic oils, glucosteroids, vitamins and/or fatty acids in EP 0540766(publ. May 12, 93). EP 0540766 or the EP 0459432 show the protection of platelets and also the differentiation of monocytic cells by cholesterol and LDL including modulation of cAMP. In addition, the saturated kinetics of cellular acetylhydrolases (phospholipases) are shown with EP 540766 as well as the LDL-mediated increase of acetylhydrolases synthesis. The valid EP 0459432 (publ. Dec. 4, 91) covers e.g. paf antagonists during/against lipoprotein-mediated disorders including platelet aggregation mediated by LDL and LA-paf (DE4034090, publ. Apr. 30, 1992; Korth et al. Chem. Phys. Lipids 70, p. 109, 1994).

The successful treatment of "Metabolic Syndrome" that means of hyperinsulinemia is based on the differentiation data with endothelial cells in response to insulin (EP 0604830, DE 4244265, publ. Jul. 6.94; Korth et al. Biochem. Pharmacol. 49, 1793, 1995). Metabolic syndrome is mediated by LA-paf with thickening of the intima and borderline hypertension are then successfully treated using the paf antagonist WEB 2086 (Wu et al. J. Int. Med. 246, S. 389, 1999).

The protection with Ginkgoloides is shown using endothelial barriers in the presence of metabolic syndromes and/or alcohol-related hyperlipidemia (R. M. Korth, Rec. Res. Devel. Lipids, p. 61, 2001, Journal of men's health and gender, vol. 3, p, 279-289, 2006). The clinical studies confirm the before mentioned property rights which are included by citations. However, the present invention clinically surprised with novel syndromes, the hypersensitivity syndromes and/or with the before unrecognized loss of calcium, the impairments of pigmentation.

Applicant shows with the valid EP 0540767 (publ. May 12, 1993) for the first time the mental and cerebral disorders which are accompanied by an elevated level of lyso paf ("lyso paf syndromes") and showed for the first time a clear pathomechanism causing psychosis for example during S.D.A.T. Lyso paf binds to specific receptors with upregulatory outcome wherein the protein kinases C (PKC,PMA) also trigger the effects of other cerebral neurotransmitters (EP 0540767, publ. May 12, 93). Paf antagonists (also EGB 761 etc.) antagonize mental and cerebral disorders for the first time by inhibition of upregulatory lyso paf receptors so that their methods of use were claimed before in the valid EP 0540767 against psychosis, paranoid, affective, sensitive, desequilibrated, different minded, impaired characters, reactive disorders and mental borderline syndromes, which are summarized now as paranoid syndromes. The juvenile (hebe) brain (phrenia) is at especially high risk. EP 0540767 does not render obvious renal problems and alkyl-like lipids.

The applicant revealed and claimed "preparations of Ginkgoloides as mixtures" in EP0312913 (publ. Apr. 26, 89) to protect endothelial cells. The valid EP 0312913 (publ. Apr. 26, 89) manifests also EGB761 with percutaneous applications. Paf analogues were also revealed (R. Korth et al., Chem. Phys. Lipis 36, S. 209, 1985, R. Korth et al. Eur. J. Pharmcol. 152, S. 101, 1988, R. Korth, Vascular Endothelium Nato, Asi, Plenum Press, eds. Catravas et al., S. 89-98, 1989). The inhibition of Paf receptors is published on high level including the biological active ether-phospho (ryl) cholines PAF-Acether, LA-paf or lyso paf (R.-M. Korth: EP 0312913, EP 0540767, Korth et al. Eur. J. Pharmacol. 152, 101-110, 1988; Chem. Phys. Lipids 70, p. 109, 1994; R.-M. Korth et al. Biochem. Pharmacol. 49, p. 1793, 1995; R.-M. Korth, Int. Arch. All. Imm. 113, p. 460, 1997; Meade et al. Biochem. Pharmacol. 41, p. 657-668, 1991; Hwang et al. Biochim. Biophys. Acta 1085, 91-105, 1991).

In contrast, novel screening procedures led here to surprising components such as acetylating substances and to novel compositions. Novel screening procedures are specified here for the first time to select novel compositions and/or novel components in order to inhibit the unexpected harm of AAGPC including its derivatives, products (e.g. alkyl-glycerols, alkyl LPA, cannaboids, acetylacyl-CoA etc.).

The instable inflammatory mediator PAF is known as hypotensive phospholipid in other words as a negative inotropic mediator so that the objection OS DE 3929763 leads away from the present invention. PAF is negative inotrop in the objection OS DE 3929763 (publ. Mar. 14, 1991) so that paf antagonists (and magnesium) are used in the presence of "low contractile outcome of the heart . . . myocardial insufficency . . . for treatment of the lowered adrenergic stimulation of betareceptors of the heart" just because PAF is negative inotrope (OSDE3929763, p. 2, line 18-42). As PAF is negative inotrop it is hypotensive so that antagonists against PAF should have a positive inotropic outcome. The blood pressure should be raised in the presence of myocaridal insufficiency whereas the blood pressure has to be lowered here in accordance with the present invention for example during the hypersensitivity syndromes. In addition, a synergistic effect with Betablockers is desired here but not antagonistic hypertensive effect with Betablockers. Many antidementiva (e.g. cholineesterase inhibitors) cannot be combined with Betablockers so that an important different use of Ginkgoloides is shown here for the first time which is suitable for older persons who have an healthy heart with correctly treated hypertension.

The hormonal composition is novel and surprising. None of the foreign patents which are later published rendered the current compositions and/or use methods obvious. The claimed matter of third parties is left behind regarding all aspects of the present inventive matter. Those foreign patents clean again already cleanded extracts (see EP 360556, filed Sep. 19, 89 vs. EP 1037646, filed Dec. 19, 1997), but those extracts are not purified regarding ethereal volatile oils and no antioxidatively stabilized oils are used. Novelty is indicated by third parties revealing series of rather known handicraft steps to win some more percentages of ginkgolides in "special extracts" of *Ginkgo biloba* (product by process: purification/limitation etc.). The before published methods of use are final/late vascular disorders, organic cerebral disorders and/or manifest decline of cerebral outcomes while those patents do not propose any indications, therapeutical instructions for otherwise healthy persons at risk. Those manufacturing methods are not decisive here as the novel screening procedures are able to select here out of various extracts (EGB, EGB761 etc.). In addition, novel manufacturing methods are specified in detail in the priority document (P34669914) which are more suitable for oily preparations and for more reasonable preparations of the novel dietary compositions or of the novel locally acting compositions without ethereal volatile oils.

Synthetic compounds such as e.g. chlorophenyl-ether-benzodiazepine derivatives are suitable here for a novel second use directed against AAGPC, including derivatives, products as the alkylacyl-like decline of cells is clinically documented here by the additive harm of alcohol and/or nicotine consumption which was firstly treated in time. The published risk factors for example elevated levels of LDL, cholesterol and/or triglycerides (e.g. EP 751774) are not significant and do not directly induce early "OMIH"-syndrome.

Food is recommended (but not claimed) using dietary recommendation lists and self control documentations for example fish, potatoes, low fat milk-, whey products, cabbages, fennel, leek, berries, spices, herbs and the calcium-rich parsley. An especially high amount of prehormones is present e.g. in cress (Herba Nasturitii, phytosterines, alkaloide, aminoacids). Milk-, whey-products contain light-dependent hormones as known. The albumin carries about 1.2 g/l calcium which is especially important for children and adolescents during the time period of growing bones. Low fat milk-, whey-products are adjusted for example with oats comprising high amounts of amino acids, vitamins by preference vitamin K and E and provitamin A (carotine), minerals such as phosphor, iron, cobalt, zinc, aluminum, potassium and the constituents, boric acid, selene, iodide. Cellulose, corn-products containing selene are known to inhibit the reabsorbation of lipids. Also flavonoids, garlic products (*Allium sativum*) are free background art in general such as phytohormones, vitamins, allicin, cholines, iodide and many lipid-lowering compounds. Genetic risk profiles, smoking, alcohol, caffee are the known reasons to develope a hypovitaminosis. Free vitamin D is included here by citation as well (Jacobus et al., N Engl J Med 1992, 326, 1173-7). The free state of the art e.g. vitamin D in milk products is included by citation (Bolick et al. N Eng. J Med 1992; 326, 1178-81). Milk contains large amounts of peptides (e.g. albumin) and enzymes (e.g. biotin) as known.

For the first time, a psychological and intellectual equilibration of persons was related with improved lifestyle and evidence was provided. A long term healing was shown for the first time regarding impairments of soul, mind and body. Also a loss of calcium during/by albuminuria is recognized and treated here for the first time.

Moreover, novel dietary fibers (e.g. *Plantago Ovata*) are added to the novel compositions against the surprising "OMIH"-syndrome. The novel locally acting and/or dietary compositions protect for the first time against alkyl-acyl-GPC its derivatives, products against cellular hypersensitivity syndromes and decline of cells in the entire organism (e.g. AAGPC, acetylacyl-CoA, alkyl-LPA, alkyl-cannaboides, alkyl-ethanolamine etc.). Novel compositions were clinically developed consisting of purified, prepared, stabilized and/or semi-synthetic components. The compositions comprise for the first time also a mixture of Ginkgoloides with calcium (or phosphor) while up to now only antagonists against calcium were used as antihypertensiva and antidementiva and those led away from the calcium and phosphate supplements.

The psychological and intellectual conditions of human individuals are improved here for the first time by the compositions also in a hormonal manner including improved life style in accordance with the invention. There is for the first time an effect of Ginkgoloides, hormones, prehormones, minerals, constituents and/or acetylcysteines against overweight-related, hypersensitivity syndromes and/or impaired pigmentations wherein the many years of therapeutical care document here for the first time a (genetic) regeneration of all cells in the entire organism.

BRIEF DESCRIPTION OF THE DRAWINGS

FIG. 5 shows that platelets specifically bound [$^3$H]acetyl paf at 4° C. in a concentration-dependent manner (A: 0.65 nM; B: 0.065 nM). Unlabeled paf (50 nM) competed showing specific binding of [$^3$H]acetyl paf. The low non-specific binding did not increase. Next, [$^3$H]alkyl-paf failed binding to stiffened platelets at 4° C. showing moderate specific binding only at 20° C. (C: 0.65 nM, 30 min, 20° C.). These data showed that stiffening of platelets antagonized relevant specific binding of [$^3$H]alkyl groups indicating allosteric upregulation. Values are expressed as bound labelled ligands to $10^8$ platelets. Platelets were separated with vacuum filtration and means±1 S.D. are from three experiments.

FIG. 6 shows the concentration-dependent inhibition of bound [$^3$H]alkyl-paf after addition of Ginkgolide BN 52021 (30 min 20° C.). Platelets were treated with formaldehyde (1%, 30 min, n=6). Values are expressed as bound [$^3$H]alkyl-paf to $10^0$ platelets. Means±1 S.D. are from three experiments.

FIG. 7 shows that bound [$^3$H]alkyl-paf to stiffened platelets was inhibited at low concentrations of unlabeled synthetic paf (·) or with biological paf (o) or with WEB 2086 (<). Binding of [$^3$H]alkyl-paf was inhibited by biological paf extracted from whole blood without subsequent HPLC-separation. Biological paf competed with [$^3$H]alkyl-paf binding to receptors of formaldehyde-treated platelets (0.65 nM, 20° C., 30 min, n=4).

TABLE 1

Figure 1:
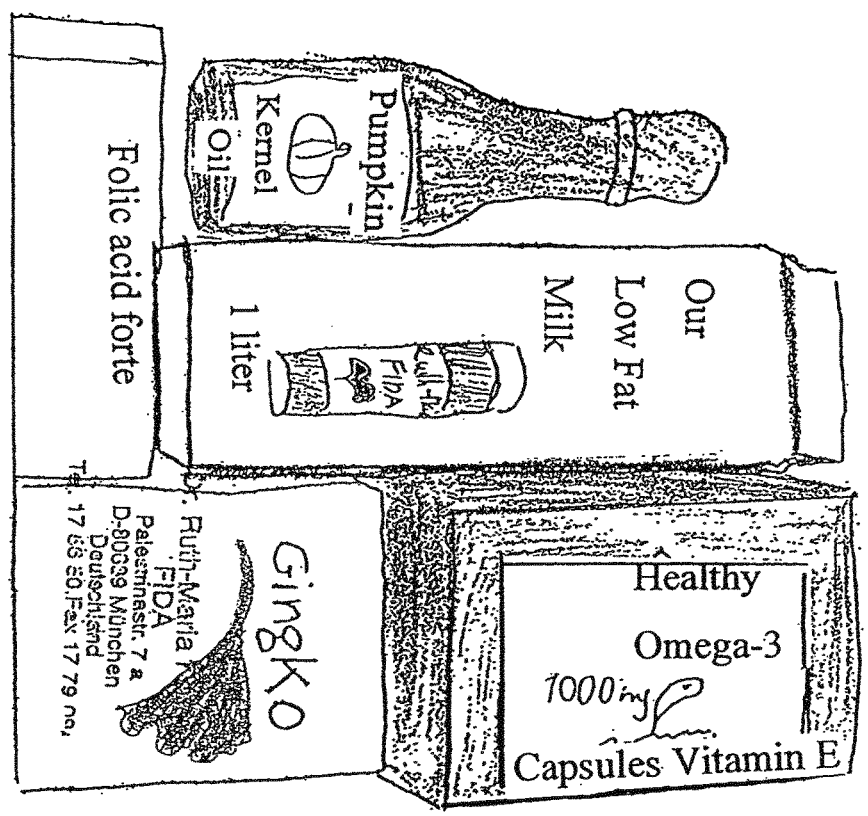
FIG. 1 shows the ingredients of the composition at baseline.
Figure 2:
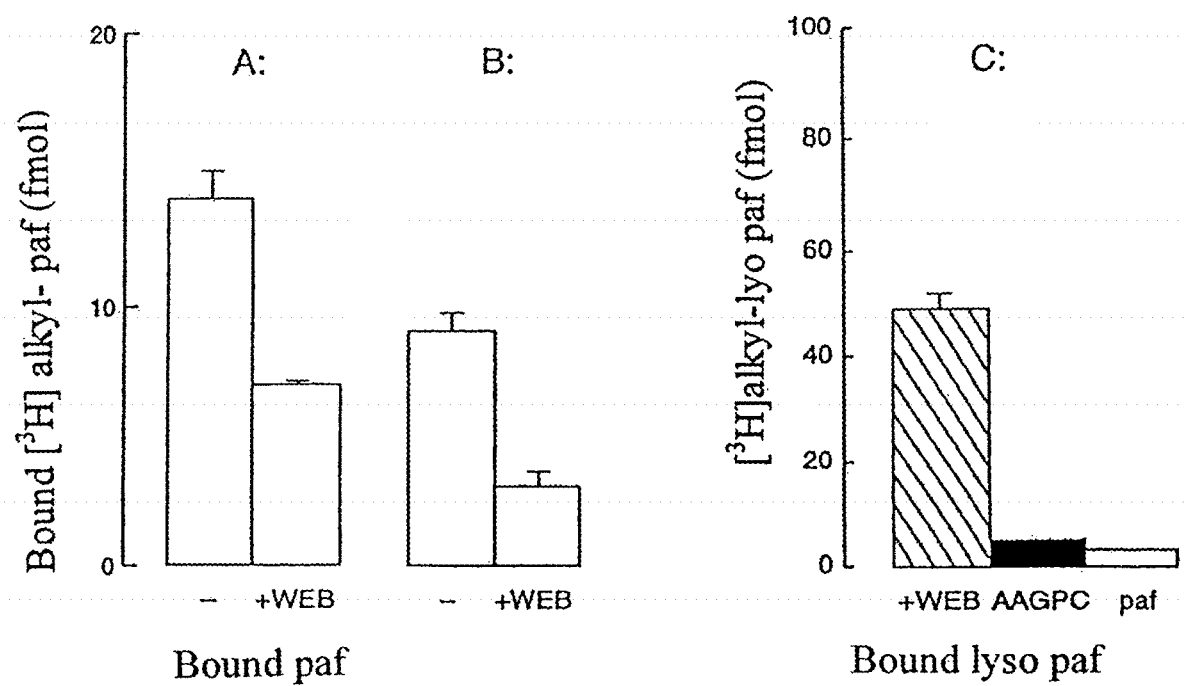
FIG. 2 shows specific and non-specific binding of [$^3$H] alkyl-paf to washed aspirinated platelets. Platelets from hyperlipidemic women (A: "OMIH"-syndrome") bound more [$^3$H]alkyl-paf and showed higher non-specific binding in the presence of the paf receptor antagonist WEB 2085 compared to platelets from normolipidemic persons (B; 0.065 nM, $10^8$ cells/ml, 30 min, 20° C.). Normolipidemic platelets bound [$^3$H]-alkyl-lyso paf (0.065 nM) in the presence of an antagonist (40 nM WEB2086) without relevant formation of indicated cellular metabolites. AAGPC and LA-paf are chemically alkyl-acyl-sn-glycero-phosphocholines. Normolipidemic platelets do not incorporate [$^3$H] alkyl-lyso paf and do not form AAGPC in the presence of the Ginkgoloides (WEB) and of free, delipidated albumin (0.25% BSA, FIG. 2C). Values are fmol per $10^8$ platelets and are means±1 S.D. from three different experiments as described (R. Korth et al. Chem. Phys. Lipids 70(1994), 109-119).
Figure 3:
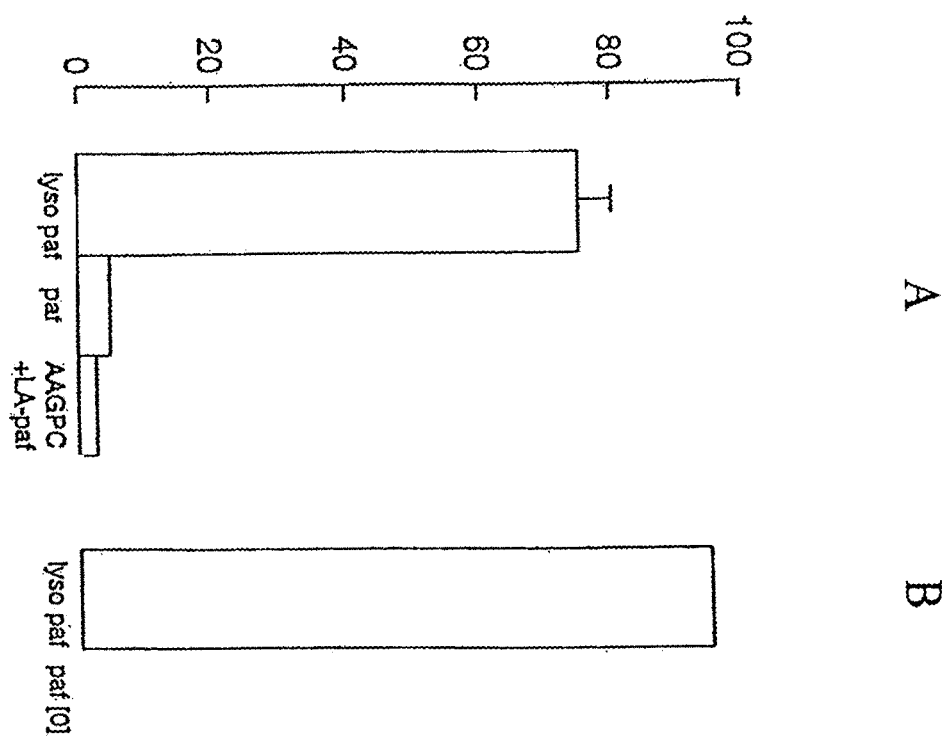
FIG. 3 shows that intact human platelets bound [$^3$H]alkyl-lyso paf (A: 0.065 nM) and did not metabolize [$^3$H]alkyl-lyso paf to labeled AAGPC and/or LA-paf. [$^3$H]alkyl-lyso paf was stable in the albumin buffer as well (B: 0.25% BSA, 30 min, 20° C.). Next, [$^3$H]alkyl-paf (0.65 nM) was added and catabolized to [$^3$H]alkyl-lyso paf in the presence of apo B (0.1 mg/ml, Sigma Chemical) or purified VLDL (D: 80 µg/ml) and only addition of purified LDL (E: 95 µg/ml) triggered formation of AAGPC and LA-paf. Addition of purified HDL did not form relevant amounts of cellular AAGPC-LA-Paf (F: 85 µg/ml). These data indicated that acetylhydrolases of LDL and/or VLDL form [$^3$H]alkyl-lyso paf. Overall, purified LDL-particles rather than isolated apoB trigger uptake and formation of AAGPC and/or LA-paf. Values are expressed as percent of added label bound to platelets. Cells were separated using vacuum filtration as described (R. Korth et al. Chem. Phys. Lipids 70, 109-119, 1994). Values were expressed as percent of added label. Values are means±1.S.D. of three different experiments.
Figure 3:
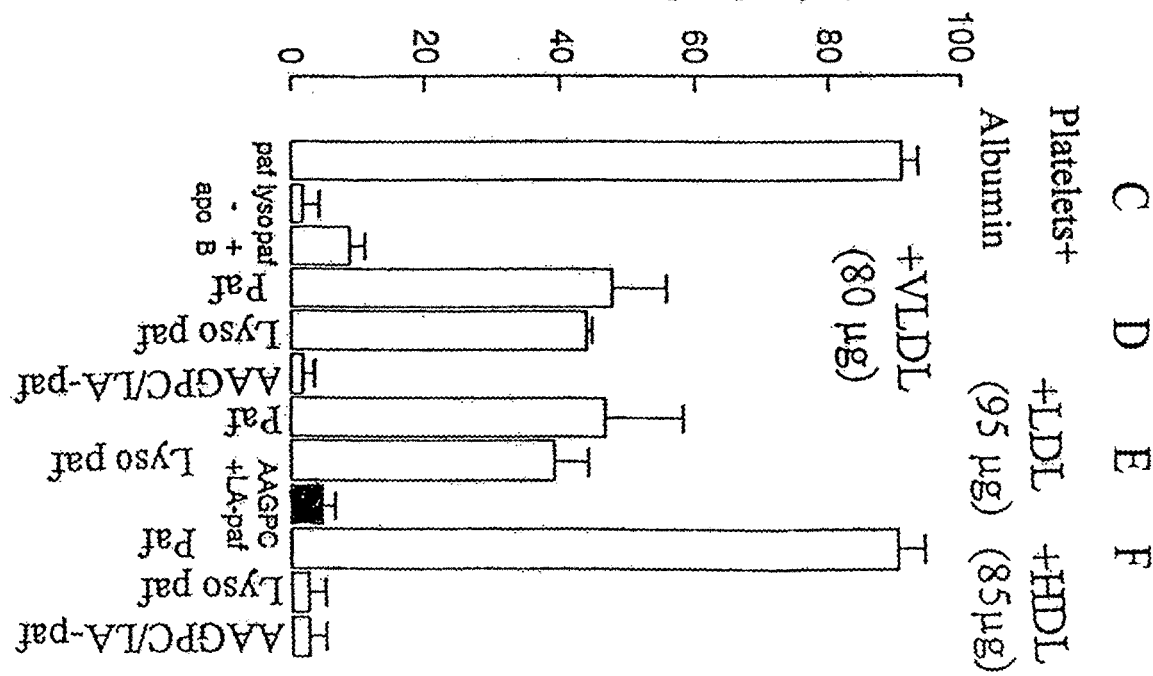
Figure 4:
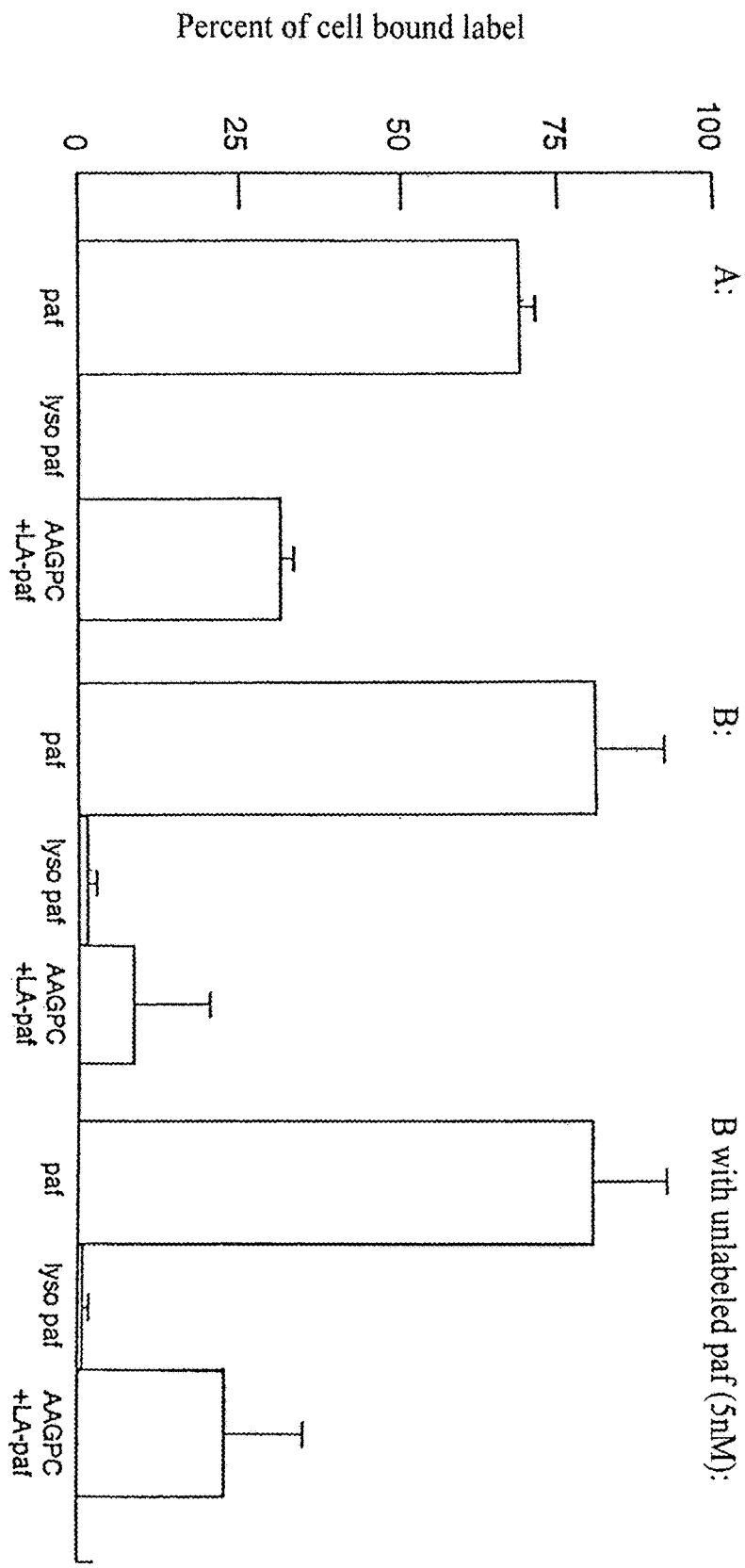
FIG. 4 shows that human neutrophils formed labeled AAGPC+LA-paf. Washed intact cells were incubated with normal or excess concentrations of [$^3$H]-alkyl-paf forming then the stable amount of AAGPC & LA (A: 0.65 nM or B: 6.5 nM). Unlabeled paf (5 nM) did not compete with formation of AAGPC/LA-paf. These data showed a saturated carrier that means at least one non-specific transport and/or binding protein (e.g. acetylhydrolase). Values are expressed as percent of added label ($2.5 \times 10^6$ cells/500µl, 0.25% BSA, n=3, see R.-M. Korth, Int. Arch. All. Imm. 113, p 460-464, 1997). Purified albumin protected here intact cells as representative non-specific antagonist.
Figure 5:
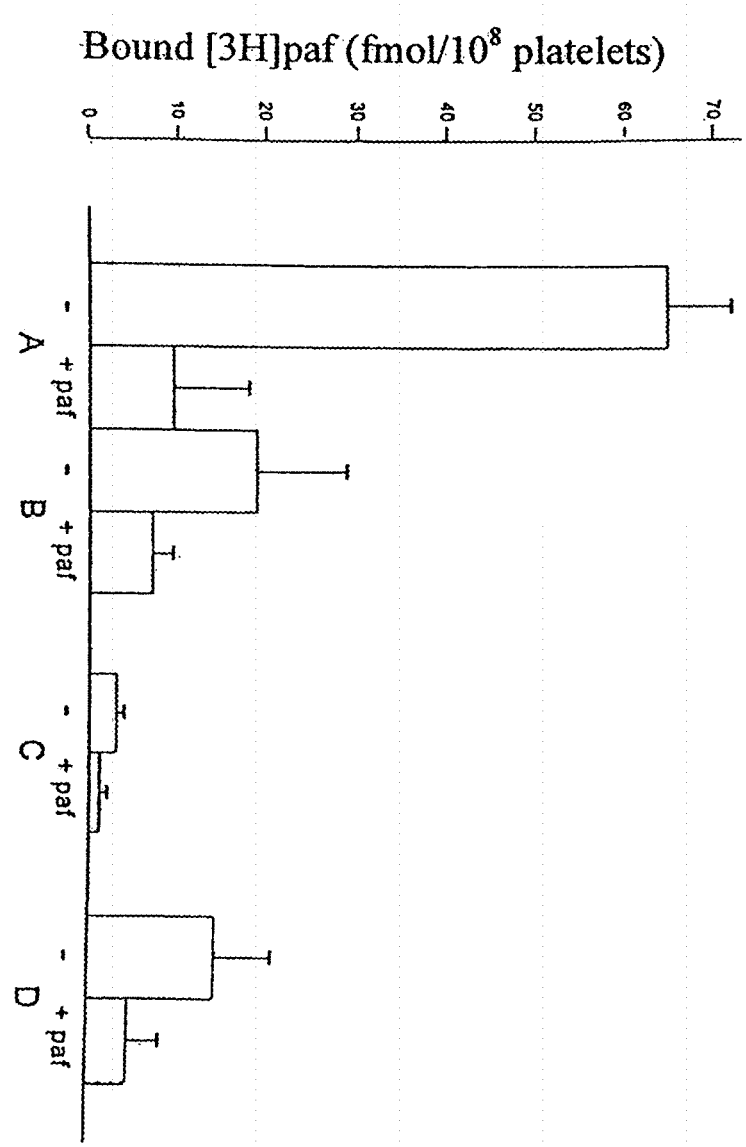
FIGS. 5 to 7 investigated for the first time binding of [$^3$H]alkyl-paf or [$^3$H]acetyl group after treatment with formaldehyde (1%, 30 min) comparing different temperatures, indicated concentrations and said Ginkgoloides. The allosteric binding of [$^3$H]alkyl groups was reached only at 20° C. while [$^3$H]acetyl groups bound at 4° C. excluding allosteric effects. Said Ginkgoloides specifically inhibited [$^3$H]-alkyl-paf binding as representative specific antagonists.
Figure 6:
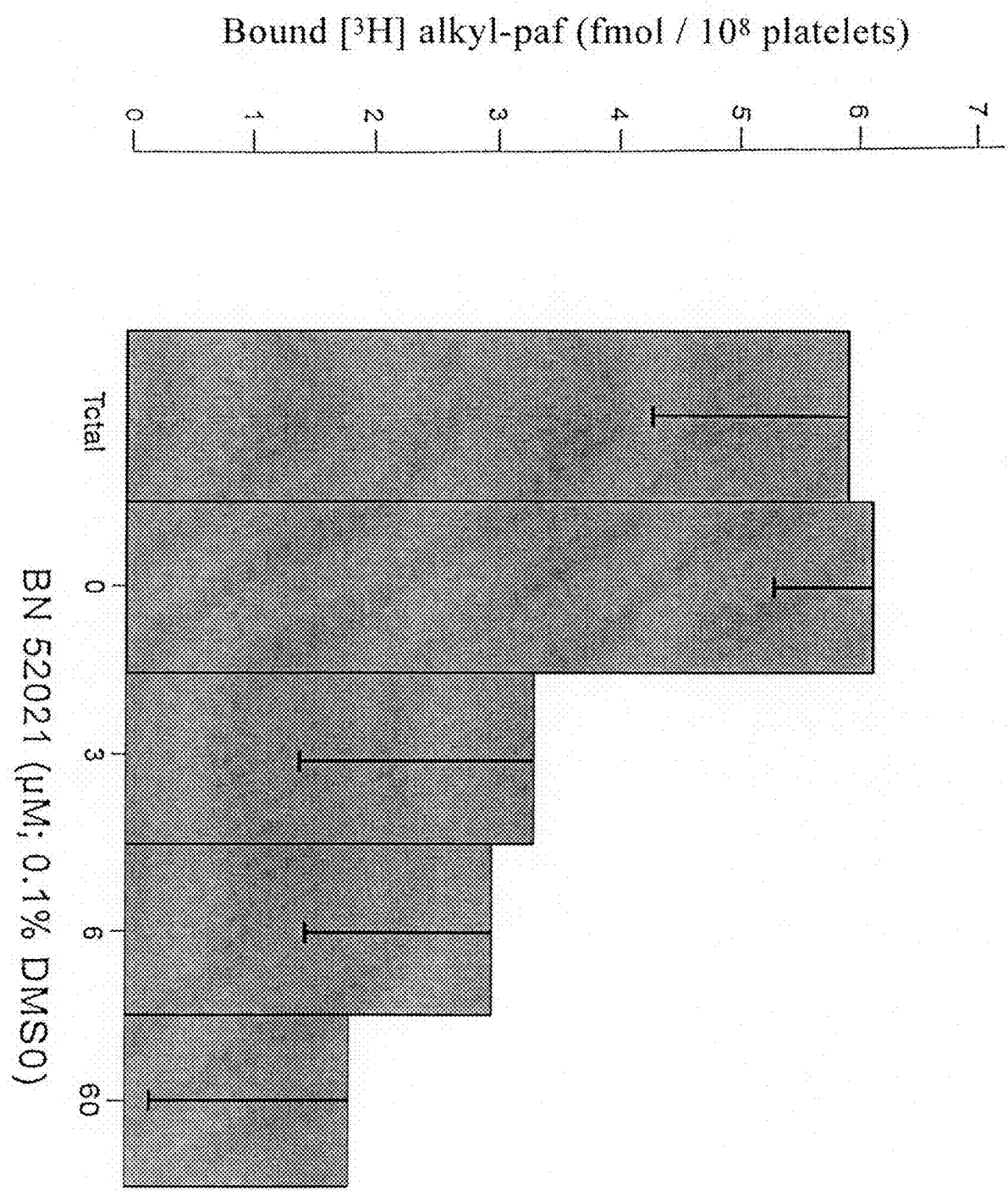
Figure 7:
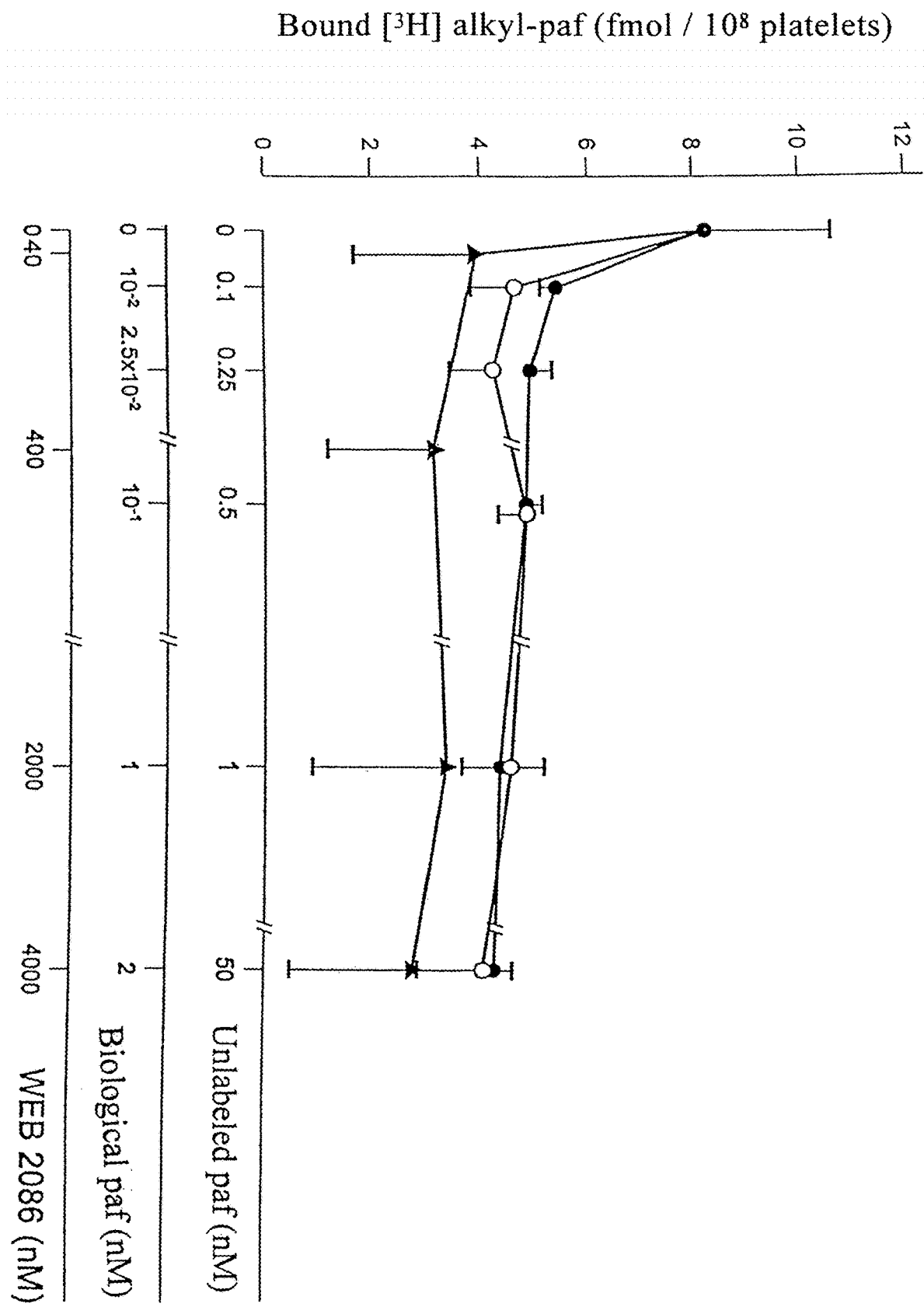

The long term healing is shown with the compositions of the invention. An abstinent "Rosenkavalier" was repaired subsequently to hepatorenal insufficiency, alcohol abuse, liver cirrhosis, ascites, esophagus varices before/until July 2001.

| Symptoms | 2001 (July) "AHA" | | 2002/2004 | 2004/2005 |
|---|---|---|---|---|
| Body weight kg/m2 | 21 ± 2 | | 28 ± 0.2 | 31 ± 1 |
| Blood pressure, mmHg, n = 1 | 148 ± 10/92 ± 6 | >130/85 | 130 ± 8/84 ± 6 | 130 ± 7/83 ± 4 |
| | Urine testings, n = 3 | | | |
| Albuminuria mg/l | 47 ± 9 | <20 mg/l | 23 ± 12 | 23 ± 6 |
| Proteinuria | + | | + | (+) |
| Hematuria | + | | excluded | excluded |

TABLE 1-continued

The long term healing is shown with the compositions of the invention. An abstinent "Rosenkavalier" was repaired subsequently to hepatorenal insufficiency, alcohol abuse, liver cirrhosis, ascites, esophagus varices before/until July 2001.

| Symptoms | 2001 (July) | "AHA" | 2002/2004 | 2004/2005 |
|---|---|---|---|---|
| Pathol. Casts | + | | excluded | excluded |
| Edema, Ascites | + | | excluded | excluded |
| Clinical Chemistry, 12 h Fasting | | | | |
| Erythrocyts/μl ×10 <4.5 | 3.6 ± 0.4 | | 3.8 ± 0.5 | 4 ± 0.5 |
| Hemoglobin g/l, | 11.5 ± 1.2 | <14 | 13.5 ± 0.9 | 15 ± 0 |
| Hematocrit % HK | 34.8 ± 3.8 | <42 | 37.5 ± 4 | 44 ± 0 |
| Corp. Vol., MCV, fl | 96.9 ± 1.3 | >95 | 100.1 ± 3.9 | 102 ± 2 |
| Corp. HK, MCH, pg | 32.1 ± 0.4 | >32 | 34.7 ± 1.2 | 35 ± 1 |
| Thrombocytes/μl ×100 | 475 ± 83 | >440 | 307 ± 59 | 177 ± 164 |
| Albumin g/l | 3.5 ± 0.1 | <4.0 | 4.4 ± 1 | 4 ± 1 |
| Cholinesterase U/l | 1657 ± 235 | <5320 | 9278 ± 1138 | 8061 ± 211 |
| Gamma-GT U/l | 39.6 ± 6.6 | >28 | 56 ± 4 | 107 ± 25 |
| Triglycerides mg/dl | 129 ± 45 | | 178 ± 36 | 166 ± 20 |
| Albumin/Triglycerides | 21 ± 3 | | | 25 ± 1 |
| LDL mg/dl | 155 ± 10 | | 194 ± 31 | 181 ± 4 |
| HDL mg/dl | 26 ± 5 | <35 | 60.3 ± 11.7 | 74 ± 8 |
| Blood glucose mg/dl | 88 ± 12 | | 80 ± 19 | 97 ± 0 |
| C-react. Prot, CRP mg/dl | 4.5 ± 0.9 | >0.5 | 1.0 ± 0.1 | 0.3 ± 0 |
| Plasmacreatinine mg/dl | 0.9 ± 0.1 | | 1.3 ± 0.3 | 0.8 ± 3 |

TABLE 2

Risk prediction of "OMIH"-syndrome. Overweighted persons show significant (*$p \leq 0.05$) or relevant ($p \leq 0.1$) impairments using multivariate modelling especially during critical lipid profiles and critical lifestyle (n = 68, ±1 S.D.)

| | Testings: | | | | | | | | |
|---|---|---|---|---|---|---|---|---|---|
| Symptoms: | 1) Glukose-intolerance | 2) LDL-Rise | 1 + 2 LDL-IGTT | 3) Triglycerid-Rise | 2 + 3 LDL-Trig. | 4) pathol. Urin l.g.Albuminuria | 5) Hormone2 p > 0.1, n.s. | 6) Alkohol | Nikotin |
| LDL-IGTT | | | | | | p = 0.081 | | | |
| Raised systol. RR | p = 0.09 | | *p = 0.047 | p = 0.054 | | | | | |
| Raised diastol. RR | | | | p = 0.044 | *p = 0.011 | | | | |
| Smoking | | | | p = 0.14 | | | | | |
| Alcohol problems | | | | p = 0.13 | | *p = 0.044 | | | |
| Fasting glucose | p = 0.08 | | p = 0.069 | | | p = 0.064 | | | |
| High Cholesterol | | *p = 0.005 | | p = 0.064 | | | | | |
| Aging | | *p = 0.028 | | | | | | | |
| Raised BMI | | | | p = 0.066 | | | | *p = 0.011 | p = 0.1 |
| Pathol. Urines | | | | p = 0.069 | p = 0.069 | | | | |

TABLE 3

Follow-up of "OMIH"-syndromes. Initially stated weight problems (BMI1 + BMI2), critical lipid profiles, critical lifestyle were significantly associated with impairments, namely with albuminuria and/or raised blood pressure (*$P \leq 0.05$, ±1 S.D).
Study groups:
Cases: 99/n = 153, 04/n = 1:

| | BMI1 | | "OMIH" | BMI2 | | AHA1 | |
|---|---|---|---|---|---|---|---|
| | until 99, n = 17 | until 04, n = 14 | | until 99, n = 16 | until 04, n = 10 | until 99, n = 21 | until 04, n = 14 |
| BMI kg/m2: | 27 ± 1 | 27 ± 1 | | 33 ± 3 | 32 ± 2 | 27 ± 5 | 26 ± 4 |
| Alcohol, % | 29 | 29 | | 56 | 10 | 100 | 100 |
| LDL mg/dl: | 139 ± 5 | 166 ± 58 | | 154 ± 53 | 151 ± 65 | 160 ± 61 | 131 ± 32 |
| Triglycerides mg/dl: | 123 ± 51 | 166 ± 114 | | 179 ± 109 | 145 ± 61 | 157 ± 95 | 124 ± 45 |
| Age, years | 31 ± 13 | 50 ± 19* | | 35 ± 15 | 36 ± 11 | 35 ± 14 | 42 ± 11 |
| Systol.RR, mmHg: | 124 ± 24* | 142 ± 24* | | 142 ± 20* | 135 ± 20* | 137 ± 22* | 127 ± 15 |
| Diastol.RR mmHg: | 82 ± 14 | 92 ± 11* | | 96 ± 14* | 91 ± 16* | 92 ± 11 | 88 ± 11 |
| e.g. Albuminuria, % | 29 | 50* | | 31 | 0 | 52* | 50* |

TABLE 4

Hypersensitivity syndrome during nicotine consumption, borderline-LDL,
overweight, intake of hormones (thyroid hormones, ±1 S.D.).
Hematuria and tendency to diabetes healed after equilibration of mentality and mind, improved lifestyle.

| | Follow-up: | | | | |
|---|---|---|---|---|---|
| | Strumectomy 1992 | post op 1992 | post op 1993-1995 | post op 1996-2000 | post op 2001-2006 |
| TSH, µU/ml | 0.27 ± 0.04 | 8.73 > 3.5 | 1.43 = 0.3 | 1.56 ± 0.7 | 1.0 ± 0.13 |
| Cholesterol mg/dl | 217 | 240 | 233 ± 7 | 243 ± 26 | 249 ± 13 |
| LDL, mg/dl | 155 | 177 | 155 ± 5 | 144 ± 27 | 163 ± 13 |
| HDL, mg/dl | 64 | 64 | 64 ± 7 | 68 ± 5 | 61 ± 7 |
| LDL/HDL | 2.4 ± 0.1 | 2.4 ± 0.1 | 2.5 ± 0.1 | 2.3 ± 0.3 | 2.7 ± 0.2 |
| Triglycerides mg/dl | 92 | 131 | 117 ± 20 | 90 ± 13 | 133 ± 38 |
| Fasting Glucose, mg/ld | 94 | 103 | 99 ± 64 | 86 ± 2 | 85 ± 1 |
| RR, mmHg | 120/80 | 120/80 | 120/80 | 110/70 | 120/80 |
| Hematuria: | 50 Ery/µl | 50 Ery/µl | 50 Ery/µl, n = 3 | 20 ± 26 Ery/µl | 0 Ery, n = 8 |
| Cigarettes per day | 20/day | 20/day | 20/day | 20/day | 6/day |

The invention claimed is:

1. A stable cosmetic, dermatic composition for topical and transdermal administration comprising liposomes containing antioxidant stabilized lecithins, acetylcysteine and one or more transport proteins selected from the group consisting of albumin and acetylhydrolases, such that antioxidants stabilized lecithins arrange themselves as liposomes encoating acetylated peptides/albumin of the core, wherein the composition further comprises a sun screening agent, wherein no ethereal volatile oils, perfumes and/or fatty alcohols are added to the composition, and wherein the antioxidant is vitamin e.

2. The cosmetic, dermatic composition according to claim 1 further comprising unsaturated fatty acids bound in the antioxidant stabilized lecithins of the albumin encoated with the liposomes, wherein the composition protects the skin, skin tissue and subcutaneous tissue strengthens the sun protection system of the skin and reaches melanocytes, ceratinocytes and neuronal cells.

3. The cosmetic, dermatic composition according to claim 1 further comprising Ginkgolides and at least one selected protein in liposomes as carrier of lipophilic Ginkgolides, wherein the composition is effective at protecting cells against alkyl-acyl-GPC and alkyl lipids, protecting against allosteric upregulation of cells and against impaired pigmentation.

4. The cosmetic, dermatic composition according to claim 1 wherein the composition further comprises protective albumin as at least one transport protein in liposomes as carrier of lipophilic Ginkgolides, wherein the protective albumin is obtained from milk products, from fungal products, from microorganism, cell lines or from bacteria and further contains antioxidant stabilized lecithins bound to the albumin in liposomes and wherein the lecithins are obtained from purified natural products, fish products, whey products and honey products.

\* \* \* \* \*